(12) United States Patent
Abele et al.

(10) Patent No.: US 9,938,244 B2
(45) Date of Patent: Apr. 10, 2018

(54) PROCESS FOR MANUFACTURING PYRIMIDINE SULFAMIDE DERIVATIVES

(71) Applicant: IDORSIA PHARMACEUTICALS LTD, Allschwil (CH)

(72) Inventors: Stefan Abele, Allschwil (CH); Jacques-Alexis Funel, Allschwil (CH); Ivan Schindelholz, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 5 days.

(21) Appl. No.: 15/118,046

(22) PCT Filed: Feb. 13, 2015

(86) PCT No.: PCT/EP2015/053047
§ 371 (c)(1),
(2) Date: Aug. 10, 2016

(87) PCT Pub. No.: WO2015/121397
PCT Pub. Date: Aug. 20, 2015

(65) Prior Publication Data
US 2016/0368882 A1   Dec. 22, 2016

(30) Foreign Application Priority Data
Feb. 14, 2014   (EP) ..................... 14155137

(51) Int. Cl.
*C07D 239/56* (2006.01)
*C07D 401/12* (2006.01)
*C07D 239/34* (2006.01)

(52) U.S. Cl.
CPC ......... *C07D 239/56* (2013.01); *C07D 239/34* (2013.01); *C07D 401/12* (2013.01)

(58) Field of Classification Search
CPC .................................................. C07D 403/12
See application file for complete search history.

(56) References Cited

U.S. PATENT DOCUMENTS

| | | | |
|---|---|---|---|
| 7,094,781 B2 | 8/2006 | Bolli et al. | |
| 7,285,549 B2 | 10/2007 | Bolli et al. | |
| 7,323,465 B2 | 1/2008 | Bolli et al. | |
| 8,324,232 B2 | 12/2012 | Bolli et al. | |
| 9,422,249 B2 | 8/2016 | Abele et al. | |
| 2011/0082151 A1* | 4/2011 | Rao ..................... | A61K 31/497 514/250 |

FOREIGN PATENT DOCUMENTS

| WO | WO 02/053557 A1 | 7/2002 |
|---|---|---|
| WO | WO 03/055863 A1 | 7/2003 |

(Continued)

OTHER PUBLICATIONS

IP.com Journal (2014), 14(2A), 1-11 (IPCOM000234588D) (Jan. 21, 2014).*

(Continued)

*Primary Examiner* — Alexander R Pagano
(74) *Attorney, Agent, or Firm* — Arent Fox LLP

(57) ABSTRACT

The invention relates to a process for manufacturing the compound of formula I

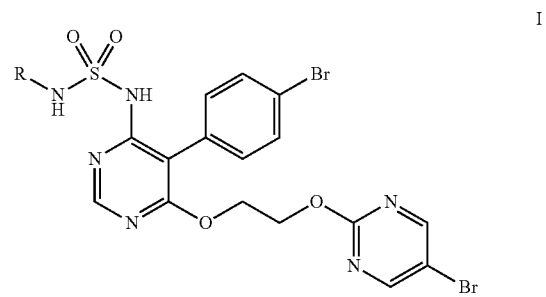

wherein R is H, $(C_1-C_6)$alkyl or benzyl, or a salt thereof, said process comprising the reaction of the compound of formula I-1

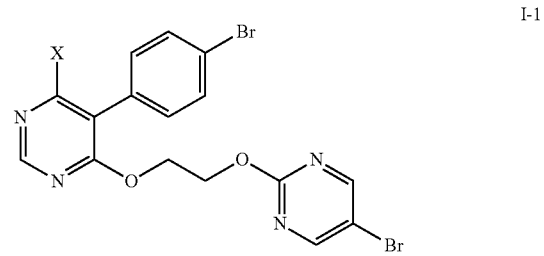

wherein X is Br, Cl or F, or a salt thereof, with the compound of formula I-2

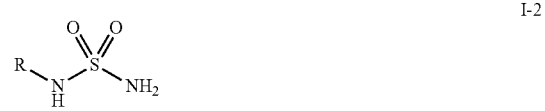

wherein R is H, $(C_1-C_6)$alkyl or benzyl, or a salt thereof, in the presence of a base, and, when X is Br or Cl, in the presence of tetra-n-butyl ammonium fluoride hydrate or cesium fluoride. The invention further relates to the compound of formula I-1 and uses thereof.

21 Claims, No Drawings

(56) References Cited

FOREIGN PATENT DOCUMENTS

| WO | WO 2009/024906 A1 | 2/2009 |
| WO | WO 2010/091824 A1 | 8/2010 |
| WO | WO 2014/155304 A1 | 10/2014 |

OTHER PUBLICATIONS

M. Iglarz et al., 227 The Journal of Pharmacology and Experimental Therapeutics, 736-745 (2008).*
Bolli et al., "The Discovery of N-[5-(4 Bromophenyl)-6-[2-[(5-bromo-2-pyrimidinyl)oxy]ethoxy]-4pyrimidinyl]-N'-propylsulfamide (Macitentan), an Orally Active, Potent Dual Endothelin Receptor Antagonist," J. of Med Chem., 2002, pp. 7849-7861.
International Search Report issued in International Patent Application No. PCT/EP2015/053047 dated Mar. 30, 2015.
Kokatla et al., "One-Pot Etherification of Purine Nucleosides and Pyrimidines," Organic Letters, vol. 12, 2010, pp. 4478-4481.
March's Advanced Organic Chemistry, Reactions, Mechanisms and Structures, Sixth Edition (2007), pp. 864-867.
International Preliminary Report on Patentability issued in International Patent Application No. PCT/EP2015/053047, dated Feb. 8, 2016 (18 pages).
Written Opinion issued in International Patent Application No. PCT/EP2015/053047, dated Mar. 30, 2015 (5 pages).

\* cited by examiner

PROCESS FOR MANUFACTURING PYRIMIDINE SULFAMIDE DERIVATIVES

CROSS REFERENCE TO RELATED APPLICATION

This application is a 35 U.S.C. 371 National Phase of PCT Application No. PCT/EP2015/053047, filed Feb. 13, 2015 which claims priority to European Patent Application No. 14155137.4, filed Feb. 14, 2014. The disclosure of these prior applications are hereby incorporated in their entirety by reference.

The present invention relates to a process for manufacturing the pyrimidine sulfamide derivatives of formula I

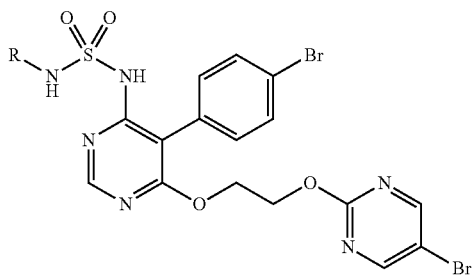

wherein R represents H, $(C_1-C_6)$alkyl or benzyl.

The compounds of formula I are endothelin receptor antagonists which have been first disclosed in WO 02/053557. Among these compounds, macitentan (compound of formula I wherein R is n-propyl; chemical names: N-[5-(4-bromophenyl)-6-[2-[(5-bromo-2-pyrimidinyl)oxy]ethoxy]-4-pyrimidinyl]-N'-propylsulfamide or N-[5-(4-bromophenyl)-6-{2-[(5-bromopyrimidin-2-yl)oxy]ethoxy}pyrimidin-4-yl]-N'-propylsulfuric diamide) is an endothelin receptor antagonist that is notably approved by the US Food and Drug Administration and the European Commission for the treatment of pulmonary arterial hypertension. The last step of one of the potential preparation routes described in WO 02/053557, called "Possibility A" and "Possibility B", can be summarised as shown in Scheme A1 hereafter.

Scheme A1

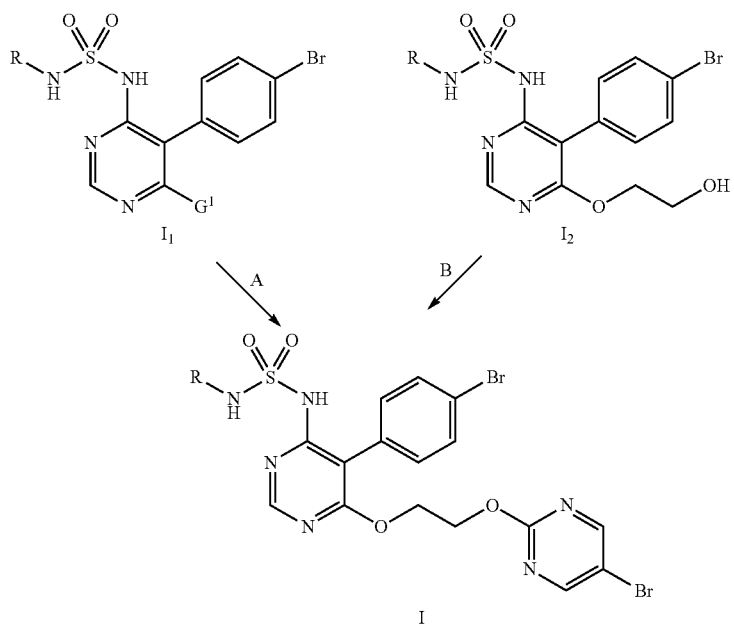

In Scheme A1, $G^1$ represents a reactive residue, and preferentially a chloro atom.

The preparation of macitentan according to "Possibility B" of WO 02/053557 has furthermore been described in Bolli et al., *J. Med. Chem.* (2012), 55, 7849-7861. Accordingly:

KOtBu was added to a solution of a large excess ethylene glycol in dimethoxyethane and the compound of formula $I_1$ wherein $G^1$ is Cl (see Scheme A1 above) was added thereto; after heating at 100° C. for 70 h, work-up involving extraction and purification by column chromatography, the compound of formula $I_2$ was obtained in a 86% yield; and The compound of formula $I_2$ was added to a suspension of NaH in THF, the mixture was stirred and diluted with DMF before 5-bromo-2-chloropyrimidine was added; after heating at 60° C. and work-up involving extraction and crystallisation steps, macitentan was obtained in a 88% yield.

The methods for manufacturing macitentan described above are however not appropriate for manufacturing macitentan in a sufficient purity unless numerous purification steps are undertaken to remove the impurities, including ethylene glycol, from the compound of formula $I_2$ before performing the step corresponding to "Possibility B" of WO 02/053557. In this regard, it should be mentioned that ethylene glycol is actually harmful and rather difficult to remove by distillation due to a high boiling point.

Besides, the compound of formula I wherein R is H has been disclosed in WO 2009/024906. The last steps of the potential preparation routes described in WO 2009/024906 can be summarised as shown in Scheme A2 hereafter.

electronic effects, thus rendering a nucleophilic aromatic substitution unlikely.

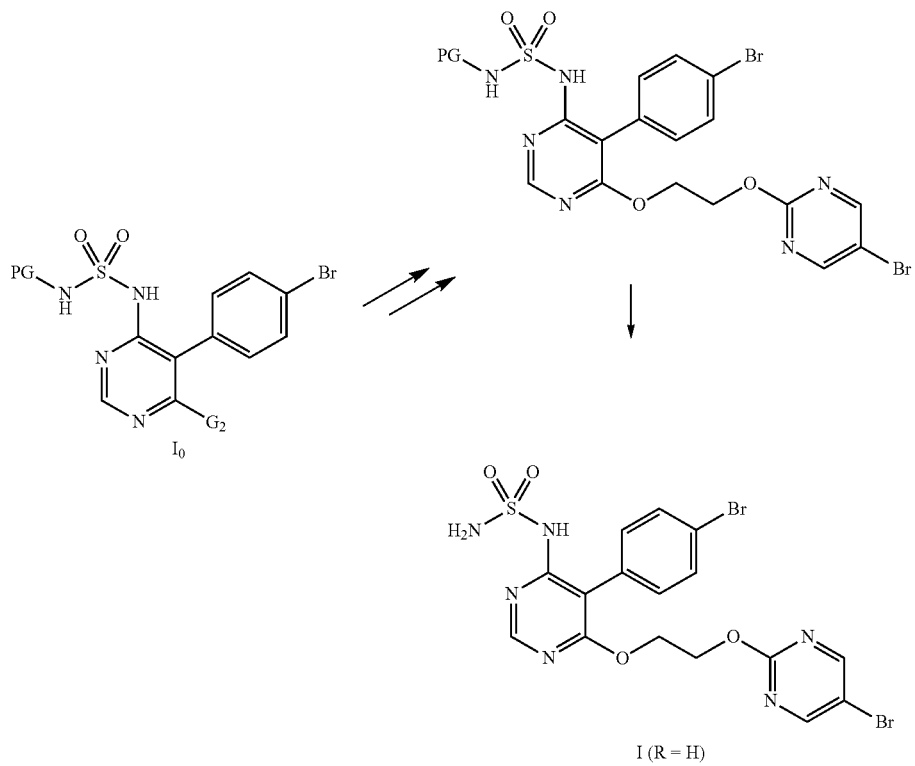

Scheme A2

In Scheme A2, $G_2$ represents a reactive group such as a halogen atom (preferably a chlorine atom) and PG represents a protecting group such as a benzyl group or a 4-methoxy- or a 2,4-dimethoxybenzyl group.

According to the route disclosed in WO 2009/024906 (see Scheme A2), the compound of formula $I_0$ can be reacted with ethylene glycol in the presence of a base, in the presence or absence of an additional solvent and preferably at elevated temperatures. The resulting intermediate can then be reacted with 5-bromo-2-chloropyrimidine or an equivalent reactive entity in the presence of a strong base in a solvent such as THF, DMF, dioxane, etc. or mixtures thereof. The protecting group PG can then be removed by standard methods to yield the compound of formula I wherein R is H.

The manufacturing route disclosed in WO 2009/024906, which could also be tried with PG=Fmoc or PG=Boc, has again the drawback of using ethylene glycol in one of its late stages.

While the manufacturing routes using ethylene glycol in one of the final stages have known drawbacks, one skilled in the art would however not know any true alternative route offering a reasonable expectation of success. In particular, the skilled artisan would expect that the reaction shown in Scheme 0 below, wherein X represents a halogen atom such as fluorine, bromine or chlorine and R represents hydrogen or alkyl is not likely to proceed because the pyrimidine ring system of the compound of formula I-1 is deactivated by

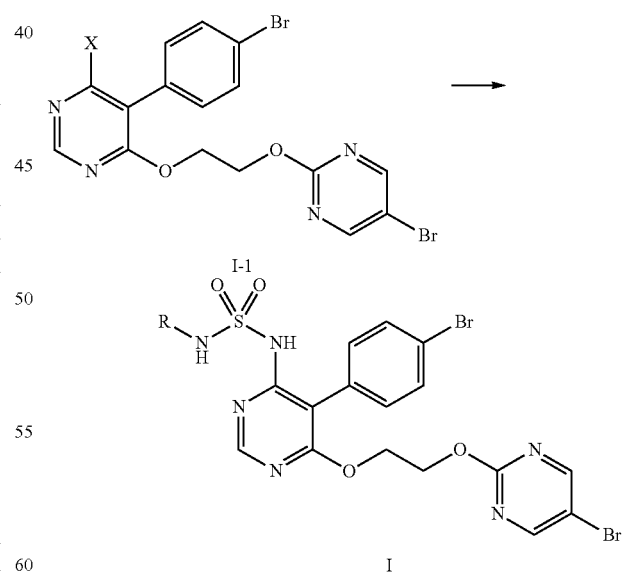

In this regard, one can for example refer to *March's Advanced Organic Chemistry* handbook (see section "Reactivity" of the chapter "Aromatic Substitution, Nucleophilic and Organometallic" in *March's Advanced Organic Chemistry, Reactions, Mechanisms and Structures*, Sixth Edition (2007), 864-867). The skilled artisan thus knew that the compound of formula I-1 is deactivated towards a nucleophilic aromatic substitution due to its alkoxy side chain; moreover the skilled artisan knew at the same time that sulfamide or n-propylaminosulfonamide are poor nucleophiles (mesomeric effect leading to a delocalization of the N-lone pair to the sulphur).

In accordance with the expected failure of the nucleophilic aromatic substitution reaction, the inventors could thus observe that reaction of the compound of formula I-1 wherein X is chlorine with standard fluorinating agents such as KF or NaF did not yield the fluorinated intermediate with sufficient purity and yield. Besides it was also observed that reaction of the compound of formula I-1 wherein X is chlorine with sulfamide did not occur at 70° C. in DMSO. These findings confirm the fact that the compound of formula I-1 is not suitable for nucleophilic aromatic substitution, in particular if the nucleophile intended to be used in the nucleophilic aromatic substitution is a poor nucleophile like a sulfamide.

It has now been surprisingly found that an alternative route to the compounds of formula I was nevertheless possible wherein the sulfamide function would be introduced in the last step by nucleophilic substitution on the pyrimidine core. The introduction of the sulfamide function through nucleophilic substitution on the pyrimidine core was however only possible in a satisfactory manner when using the particular reaction conditions found by the inventors and described hereafter.

Thus said alternative route required obtaining a fluorinated intermediate with high purity, which result could only be properly achieved using the fluorination agent tetra-n-butyl ammonium fluoride hydrate or cesium fluoride.

A significant advantage of this alternative route is that it allows the use in the last step of a pyrimidine derivative already possessing a functionalised side chain at position 6 (i.e. the 2-(5-bromo-pyrimidin-2-yloxy)-ethoxy side chain), which avoids the use of an excess of ethylene glycol (required at some point to obtain the 2-(5-bromo-pyrimidin-2-yloxy)-ethoxy side chain—see e.g. WO 02/053557 or Bolli et al., *J. Med. Chem.* (2012), 55, 7849-7861) in a late stage of the manufacturing process. Besides, this route allows to use a single intermediate for preparing in a single step any compound of formula I wherein R represents H, $(C_1-C_6)$alkyl or benzyl.

Various embodiments of the invention are presented hereafter:

1) The invention firstly relates to a process for manufacturing the compound of formula I

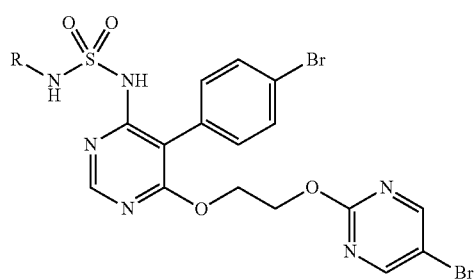

wherein R is H, $(C_1-C_6)$alkyl or benzyl, or a salt thereof, said process comprising the reaction of the compound of formula I-1

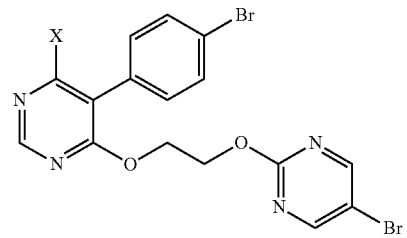

wherein X is bromine, chlorine or fluorine (and in particular chlorine or fluorine), with the compound of formula I-2

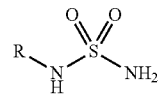

wherein R is H, $(C_1-C_6)$alkyl or benzyl, or a salt of said compound of formula I-2, said reaction being performed in the presence of a base in a polar aprotic organic solvent or a polar mixture of aprotic organic solvents, and, when X is bromine or chlorine, in the presence of tetra-n-butyl ammonium fluoride hydrate or cesium fluoride.

2) Preferably, the base used in the process according to embodiment 1) will be selected from the group consisting of NaOH, KOH, 1,8-diazabicyclo[5.4.0]undec-7-ene, triethylamine, potassium tert-butylate, $Na_2CO_3$, $K_2CO_3$ and $Cs_2CO_3$ (and notably from the group consisting of NaOH, KOH, 1,8-diazabicyclo[5.4.0]undec-7-ene, triethylamine, potassium tert-butylate, $Na_2CO_3$ and $K_2CO_3$).

3) In particular, the base used in the process according to embodiment 1) will be $K_2CO_3$.

4) Preferably, the reaction of the compound of formula I-1 with the compound of formula I-2 in the process according to one of embodiments 1) to 3) will be performed at a temperature from 20 to 140° C.

5) More preferably, the reaction of the compound of formula I-1 with the compound of formula I-2 in the process according to one of embodiments 1) to 3) will be performed at a temperature from 60 to 80° C.

6) Preferably also, the reaction of the compound of formula I-1 with the compound of formula I-2 in the process according to one of embodiments 1) to 5) will be such that 0.9 to 4 equivalents (and in particular 0.9 to 1.5 equivalents) of compound of formula I-2 are used per equivalent of compound of formula I-1.

7) More preferably, the reaction of the compound of formula I-1 with the compound of formula I-2 in the process according to one of embodiments 1) to 5) will be such that 1 to 3 equivalents (for example 1 to 1.5 equivalents and notably 1 to 1.2 equivalents) of compound of formula I-2 are used per equivalent of compound of formula I-1.

8) Besides, the reaction of the compound of formula I-1 wherein X is chlorine with the compound of formula I-2 in the process according to one of embodiments 1) to 7) will preferably be such that 1.1 to 10 equivalents of tetra-n-butyl ammonium fluoride hydrate or cesium fluoride are used per equivalent of compound of formula I-1.

9) In particular, the reaction of the compound of formula I-1 wherein X is chlorine with the compound of formula I-2 in the process according to one of embodiments 1) to 7) will be such that 2 to 4 equivalents of tetra-n-butyl ammonium fluoride hydrate or cesium fluoride are used per equivalent of compound of formula I-1.

10) Preferably also, the reaction of the compound of formula I-1 with the compound of formula I-2 in the process according to one of embodiments 1) to 9) will be such that 1.5 to 10 equivalents (and notably 1.5 to 5 equivalents) of base are used per equivalent of compound of formula I-1.

11) More preferably, the reaction of the compound of formula I-1 with the compound of formula I-2 in the process according to one of embodiments 1) to 9) will be such that 2 to 7 equivalents (and notably 2 to 4 equivalents) of $K_2CO_3$ are used per equivalent of compound of formula I-1.

12) According to a preferred embodiment of this invention, the reaction of the compound of formula I-1 with the compound of formula I-2 in the process according to one of embodiments 1) to 11) will be such that the polar aprotic organic solvent or polar mixture of aprotic organic solvents is selected from the group consisting of MeCN, chlorobenzene, iPrOAc, THF, NMP, dioxane, DMAC, DME, DMF, DMSO, sulfolane and a mixture of two solvents, whereby the first of these two solvents is selected from the group consisting of toluene and DCM and the second of these two solvents is selected from the group consisting of MeCN, chlorobenzene, iPrOAc, THF, NMP, dioxane, DMAC, DME, DMF, DMSO, sulfolane, and a mixture of toluene, DCM and a third solvent selected from the group consisting of MeCN, chlorobenzene, iPrOAc, THF, NMP, dioxane, DMAC, DME, DMF, DMSO and sulfolane.

13) Preferably, the reaction of the compound of formula I-1 with the compound of formula I-2 in the process according to embodiment 12) will be such that the polar aprotic organic solvent or polar mixture of aprotic organic solvents comprises dimethylsulfoxide.

14) More preferably, the reaction of the compound of formula I-1 with the compound of formula I-2 in the process according to embodiment 12) will be performed using dimethylsulfoxide as solvent.

15) Preferably, when the compound of formula I-1 is such that X is bromine or chlorine, the process of embodiments 1) to 14) will be performed in the presence of tetra-n-butyl ammonium fluoride hydrate.

16) In a further preferred embodiment, the process of embodiments 1) to 15) will be such X is chlorine and the reaction of the compound of formula I-1 with the compound of formula I-2 is performed in the presence tetra-n-butyl ammonium fluoride hydrate and using dimethylsulfoxide as solvent.

17) Alternatively, when the compound of formula I-1 is such that X is bromine or chlorine, the process of embodiments 1) to 14) will preferably be performed in the presence of cesium fluoride.

18) Preferably, the process of embodiment 16) will be such that 1.1 to 4 equivalents (and notably 1.1 to 1.5 equivalents or 1.1 to 1.3 equivalents) of cesium fluoride are used per equivalent of compound of formula I-1.

19) In particular, the process of embodiment 16) will be such that 2.5 to 3.5 equivalents of cesium fluoride are used per equivalent of compound of formula I-1.

20) According to one variant of the process of embodiments 1) to 19), the compound of formula I or its salt will be such that R is H.

21) According to another variant of the process of embodiments 1) to 19), the compound of formula I or its salt will be such that R is $(C_1-C_6)$alkyl.

22) Preferably, in the process according to embodiment 21), the compound of formula I or its salt will be such that R is n-propyl.

23) According to yet another variant of the process of embodiments 1) to 19), the compound of formula I or its salt will be such that R is benzyl.

24) The invention moreover relates to new synthetic intermediates useful in the preparation of the pyrimidine sulfamide derivatives of formula I, namely the compounds of formula I-1

I-1 wherein X is bromine, chlorine or fluorine, and to salts of said compounds.

25) According to one variant of embodiment 24), the compound of formula I-1 or its salt will be such that X is chlorine.

26) According to the other variant of embodiment 24), the compound of formula I-1 or its salt will be such that X is fluorine.

27) The invention further relates to the use of a compound of formula I-1 according to one of embodiments 24) to 26), or a salt thereof, in a process for manufacturing the compound of formula I as defined in embodiment 1) or a salt thereof.

28) According to one variant of embodiment 27), the compound of formula I-1 or its salt in the use of embodiment 27) will be such that X is chlorine.

29) According to the other variant of embodiment 27), the compound of formula I-1 or its salt in the use of embodiment 27) will be such that X is fluorine.

30) According to one important variant of the use of embodiments 27) to 29), the compound of formula I or its salt will be such that R is H.

31) According to another important variant of the use of embodiments 27) to 29), the compound of formula I or its salt will be such that R is $(C_1-C_6)$alkyl.

32) Preferably, in the use according to embodiment 31), the compound of formula I or its salt will be such that R is n-propyl.

33) According to yet another important variant of the use of embodiments 27) to 29), the compound of formula I or its salt will be such that R is benzyl.

34) The invention moreover relates to the use of a compound of formula I-1 according to embodiment 25), or a salt thereof, in a process for manufacturing the compound of formula I-1 as defined in embodiment 26) or a salt thereof.

35) Preferably, the use according to embodiment 34) will be such that the process for manufacturing the compound of formula I-1 as defined in embodiment 26) will comprise the reaction of the compound of formula I-1 according to embodiment 25), or a salt thereof, with tetra-n-butyl ammonium fluoride hydrate.

36) According to one variant of the use according to embodiment 35), the reaction of the compound of formula I-1 according to embodiment 25), or of a salt thereof, with tetra-n-butyl ammonium fluoride hydrate will be performed in the presence of a base.

37) Preferably, the use according to embodiment 36) will be such that the base is selected from the group consisting of NaOH, KOH, 1,8-diazabicyclo[5.4.0]undec-7-ene, triethylamine, potassium tert-butylate, $Na_2CO_3$, $K_2CO_3$ and $Cs_2CO_3$ (and in particular such that the base is selected from the group consisting of NaOH, KOH, 1,8-diazabicyclo[5.4.0]undec-7-ene, triethylamine, potassium ter t-butylate, $Na_2CO_3$ and $K_2CO_3$).

38) More preferably, the use according to embodiment 36) will be such that the base is $K_2CO_3$.

39) According to another variant of the use according to embodiment 35), the reaction of the compound of formula I-1 according to embodiment 25), or of a salt thereof, with tetra-n-butyl ammonium fluoride hydrate will be performed in the absence of a base.

40) The invention furthermore relates to a use as defined in one of embodiments 34) to 39), whereby the compound of formula I-1 thus obtained is then used for manufacturing a compound of formula I as defined in embodiment 1).

41) Preferably, the use of embodiment 40) will be such that the manufacture of a compound of formula I as defined in embodiment 1) will be performed by the reaction of the compound of formula I-1 thus obtained, or a salt thereof, with a compound of formula I-2 as defined in embodiment 2), or a salt thereof in the presence of a base in a polar aprotic organic solvent or a polar mixture of aprotic organic solvents.

42) Preferably, the base used in the process according to embodiment 41) will be selected from the group consisting of NaOH, KOH, 1,8-diazabicyclo[5.4.0]undec-7-ene, triethylamine, potassium tert-butylate, $Cs_2CO_3$, $Na_2CO_3$ and $K_2CO_3$.

43) In particular, the base used in the process according to embodiment 41) will be $K_2CO_3$.

44) According to a preferred embodiment of the use of embodiments 41) to 43), the reaction of the compound of formula I-1 with the compound of formula I-2 will be such that the polar aprotic organic solvent or polar mixture of aprotic organic solvents is selected from the group consisting of MeCN, chlorobenzene, iPrOAc, THF, NMP, dioxane, DMAC, DME, DMF, DMSO, sulfolane and a mixture of two solvents, whereby the first of these two solvents is selected from the group consisting of toluene and DCM and the second of these two solvents is selected from the group consisting of MeCN, chlorobenzene, iPrOAc, THF, NMP, dioxane, DMAC, DME, DMF, DMSO, sulfolane, and a mixture of toluene, DCM and a third solvent selected from the group consisting of MeCN, chlorobenzene, iPrOAc, THF, NMP, dioxane, DMAC, DME, DMF, DMSO and sulfolane.

45) Preferably, the reaction of the compound of formula I-1 with the compound of formula I-2 in the use according to embodiment 44) will be such that the polar aprotic organic solvent or polar mixture of aprotic organic solvents comprises dimethylsulfoxide.

46) More preferably, the reaction of the compound of formula I-1 with the compound of formula I-2 in the use according to embodiment 44) will be performed using dimethylsulfoxide as solvent.

47) As an alternative preferred embodiment, the use according to embodiment 34) will be such that the process for manufacturing the compound of formula I-1 as defined in embodiment 26) will comprise the reaction of the compound of formula I-1 according to embodiment 25), or of a salt thereof, with cesium fluoride in the presence of a base.

48) Preferably, the use according to embodiment 47) will be such that the base is selected from the group consisting of NaOH, KOH, 1,8-diazabicyclo[5.4.0]undec-7-ene, triethylamine, potassium tert-butylate, $Na_2CO_3$, $K_2CO_3$ and $Cs_2CO_3$.

49) More preferably, the use according to embodiment 47) will be such that the base is $K_2CO_3$.

50) According to a preferred embodiment of the use of embodiments 47) to 49), the reaction of the compound of formula I-1 with the compound of formula I-2 will be such that the polar aprotic organic solvent or polar mixture of aprotic organic solvents is selected from the group consisting of MeCN, chlorobenzene, iPrOAc, THF, NMP, dioxane, DMAC, DME, DMF, DMSO, sulfolane and a mixture of two solvents, whereby the first of these two solvents is selected from the group consisting of toluene and DCM and the second of these two solvents is selected from the group consisting of MeCN, chlorobenzene, iPrOAc, THF, NMP, dioxane, DMAC, DME, DMF, DMSO, sulfolane, and a mixture of toluene, DCM and a third solvent selected from the group consisting of MeCN, chlorobenzene, iPrOAc, THF, NMP, dioxane, DMAC, DME, DMF, DMSO and sulfolane.

51) Preferably, the reaction of the compound of formula I-1 with the compound of formula I-2 in the use according to embodiment 50) will be such that the polar aprotic organic solvent or polar mixture of aprotic organic solvents comprises dimethylsulfoxide.

52) More preferably, the reaction of the compound of formula I-1 with the compound of formula I-2 in the use according to embodiment 50) will be performed using dimethylsulfoxide as solvent.

53) This invention moreover relates to a process for manufacturing the compound of formula I

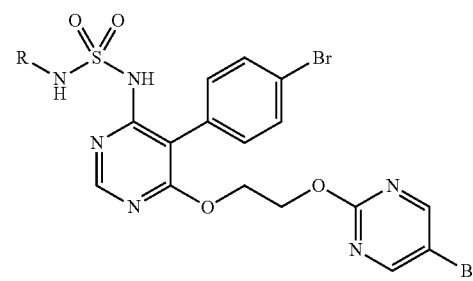

wherein R is H, $(C_1-C_6)$alkyl or benzyl, or for manufacturing a salt thereof, said process comprising the reaction of the compound of formula I-1, said process comprising the following steps:

a) the reaction of the compound of formula I-1a

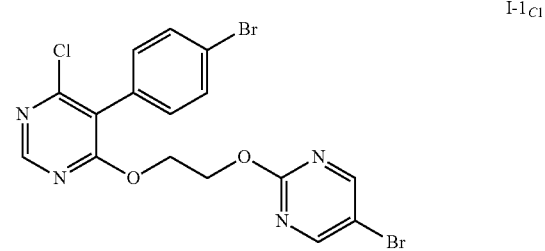 [SMILES: Clc1ncnc(OCCOc2ncc(Br)cn2)c1-c1ccc(Br)cc1]

or a salt thereof, with tetra n-butyl ammonium fluoride hydrate or cesium fluoride in the presence of a base in a polar aprotic organic solvent or a polar mixture of aprotic organic solvents, to yield the compound of formula I-1$_F$

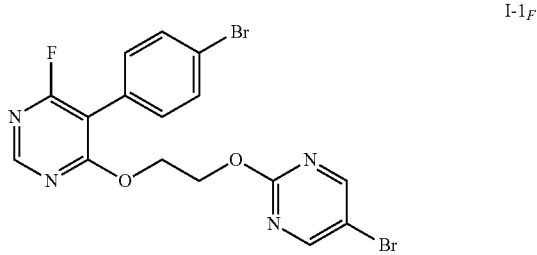 [SMILES: Fc1ncnc(OCCOc2ncc(Br)cn2)c1-c1ccc(Br)cc1]

I-1$_F$ and b) the reaction of the compound of formula I-1$_F$ obtained at step a) with a compound of formula I-2

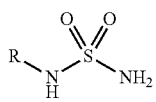

I-2 wherein R is H, (C$_1$-C$_6$)alkyl or benzyl, or a salt thereof, in the presence of a base in a polar aprotic organic solvent or a polar mixture of aprotic organic solvents, to yield said compound of formula I or a salt thereof.

54) Preferably, step a) of the manufacturing process of embodiment 53) will be performed by reacting the compound of formula I-1$_{Cl}$ with cesium fluoride.

55) Preferably, the base used in step a) of the manufacturing process of embodiment 53) or 54) will be selected from the group consisting of NaOH, KOH, 1,8-diazabicyclo[5.4.0]undec-7-ene, triethylamine, potassium tert-butylate, Na$_2$CO$_3$, K$_2$CO$_3$ and Cs$_2$CO$_3$.

56) More preferably, the base used in step a) of the manufacturing process of embodiment 53) or 54) will be K$_2$CO$_3$.

57) Preferably, the base used in step b) of the manufacturing process of one of embodiments 53) to 56) will be selected from the group consisting of NaOH, KOH, 1,8-diazabicyclo[5.4.0]undec-7-ene, triethylamine, potassium tert-butylate, Na$_2$CO$_3$, K$_2$CO$_3$ and Cs$_2$CO$_3$.

58) More preferably, the base used in step b) of the manufacturing process of one of embodiments 53) to 56) will be K$_2$CO$_3$.

59) In particular, K$_2$CO$_3$ will be used as base in both steps a) and b) of the manufacturing process of embodiment 53) or 54).

60) According to a preferred embodiment of the process according to one of embodiments 53) to 59), each of the polar aprotic organic solvent or polar mixture of aprotic organic solvents used in step a) and step b) will be independently selected from the group consisting of MeCN, chlorobenzene, iPrOAc, THF, NMP, dioxane, DMAC, DME, DMF, DMSO, sulfolane and a mixture of two solvents, whereby the first of these two solvents is selected from the group consisting of toluene and DCM and the second of these two solvents is selected from the group consisting of MeCN, chlorobenzene, iPrOAc, THF, NMP, dioxane, DMAC, DME, DMF, DMSO, sulfolane, and a mixture of toluene, DCM and a third solvent selected from the group consisting of MeCN, chlorobenzene, iPrOAc, THF, NMP, dioxane, DMAC, DME, DMF, DMSO and sulfolane.

61) Preferably, the process according to embodiment 60) will be such that each of the polar aprotic organic solvents or polar mixtures of aprotic organic solvents used in step a) and step b) will comprise dimethylsulfoxide.

62) More preferably, step a) and step b) of the process according to embodiment 60) will each be performed using dimethylsulfoxide as solvent.

63) In particular, the process according to embodiment 53) will be such that:
step a) of the manufacturing process will be performed by reacting the compound of formula I-1$_{Cl}$ with cesium fluoride, and
dimethylsulfoxide will be used as solvent in both steps a) and b).

64) Preferably, in each of steps a) and b) of the manufacturing process of embodiment 63) the base will independently be selected from the group consisting of NaOH, KOH, 1,8-diazabicyclo[5.4.0]undec-7-ene, triethylamine, potassium tert-butylate, Na$_2$CO$_3$, K$_2$CO$_3$ and Cs$_2$CO$_3$.

65) More preferably, the base will be Cs$_2$CO$_3$ in step a) of the manufacturing process of embodiment 63) or 64).

66) According to one preferred variant of this invention, the manufacturing process according to one of embodiments 53) to 65) will be such that R is n-propyl.

67) According to another preferred variant of this invention, the manufacturing process according to one of embodiments 53) to 65) will be such that R is H.

This invention thus notably relates to the manufacturing processes, the compounds and uses as defined in one of embodiments 1), 24), 27), 34) and 53) or to these manufacturing processes, compounds and uses further limited under consideration of their respective dependencies by the characteristics of any one of embodiments 2) to 23), 25) and 26), 28) to 33), 35) to 39) and 54) to 67). In particular, based on the dependencies of the different embodiments as disclosed hereinabove, the following manufacturing process, compound and use embodiments are thus possible and intended and herewith specifically disclosed in individualized form:
1, 2+1, 3+1, 4+1, 4+2+1, 4+3+1, 5+1, 5+2+1, 5+3+1, 6+1, 6+3+1, 6+5+1, 6+5+2+1, 6+5+3+1, 7+1, 7+3+1, 7+5+1, 7+5+2+1, 7+5+3+1, 8+1, 8+3+1, 8+5+1, 8+5+2+1, 8+5+3+1, 8+7+1, 8+7+3+1, 8+7+5+1, 8+7+5+2+1, 8+7+5+3+1, 9+1, 9+3+1, 9+5+1, 9+5+2+1, 9+5+3+1, 9+7+1, 9+7+3+1, 9+7+5+1, 9+7+5+2+1, 9+7+5+3+1, 10+1, 10+3+1, 10+5+1, 10+5+2+1, 10+5+3+1, 10+7+1, 10+7+3+1, 10+7+5+1, 10+7+5+2+1, 10+7+5+3+1, 10+9+1, 10+9+3+1, 10+9+5+1, 10+9+5+2+1, 10+9+5+3+1, 10+9+7+1, 10+9+7+3+1, 10+9+7+5+1, 10+9+7+5+2+1, 10+9+7+5+3+1, 11+1, 11+3+1, 11+5+1, 11+5+2+1, 11+5+3+1, 11+7+1, 11+7+3+1, 11+7+5+1, 11+7+5+2+1, 11+7+5+3+1, 11+9+1, 11+9+3+1, 11+9+5+1, 11+9+5+2+1, 11+9+5+3+1, 11+9+7+1, 11+9+7+3+1, 11+9+7+5+1, 11+9+7+5+2+1, 11+9+7+5+3+1, 12+1, 12+3+1, 12+5+1, 12+5+2+1, 12+5+3+1, 12+7+1, 12+7+3+1, 12+7+5+1, 12+7+5+2+1, 12+7+5+3+1, 12+9+1, 12+9+3+1, 12+9+5+1, 12+9+5+2+1, 12+9+5+3+1, 12+9+7+1, 12+9+7+3+1, 12+9+7+5+1, 12+9+7+5+2+1, 12+9+7+5+3+1, 12+11+1, 12+11+3+1, 12+11+5+1, 12+11+5+2+1, 12+11+5+3+1, 12+11+7+1, 12+11+7+3+1, 12+11+7+5+1, 12+11+7+5+2+1, 12+11+7+5+3+1, 12+11+9+1, 12+11+9+3+1, 12+11+9+5+1, 12+11+9+5+2+1, 12+11+9+5+3+1, 12+11+9+7+1, 12+11+9+7+3+1, 12+11+9+7+5+1, 12+11+9+7+5+2+1, 12+11+9+7+5+3+1, 13+12+1, 13+12+3+1, 13+12+5+1, 13+12+5+2+1, 13+12+5+3+1, 13+12+7+1, 13+12+7+3+1, 13+12+7+5+1, 13+12+7+5+2+1, 13+12+7+5+3+1, 13+12+9+1, 13+12+9+3+1, 13+12+9+5+1, 13+12+9+5+2+1, 13+12+9+5+3+1, 13+12+9+7+1, 13+12+9+7+3+1, 13+12+9+7+5+1, 13+12+9+7+5+2+1, 13+12+9+7+5+3+1, 13+12+11+1, 13+12+11+3+1, 13+12+11+5+1, 13+12+11+5+2+1, 13+12+11+5+3+1, 13+12+11+7+1, 13+12+11+7+3+1, 13+12+11+7+5+1, 13+12+11+7+5+2+1, 13+12+11+7+5+3+1, 13+12+11+9+1, 13+12+11+9+3+1, 13+12+11+9+5+1, 13+12+11+9+5+2+1, 13+12+11+9+5+3+1, 13+12+11+9+7+1, 13+12+11+9+7+3+1, 13+12+11+9+7+5+1, 13+12+11+9+7+5+2+1, 13+12+11+9+7+5+3+1, 14+12+1, 14+12+3+1, 14+12+5+1, 14+12+5+2+1, 14+12+5+3+1, 14+12+7+1, 14+12+7+3+1, 14+12+7+5+1, 14+12+7+5+2+1, 14+12+7+5+3+1, 14+12+9+1, 14+12+9+3+1, 14+12+9+5+1, 14+12+9+5+2+1, 14+12+9+5+3+1, 14+12+9+7+1, 14+12+9+7+3+1, 14+12+9+7+5+1, 14+12+9+7+5+2+1, 14+12+9+7+5+3+1, 14+12+11+1, 14+12+11+3+1, 14+12+11+5+1, 14+12+11+5+2+1, 14+12+11+5+3+1, 14+12+11+7+1, 14+12+11+7+3+1, 14+12+11+7+5+1, 14+12+11+7+5+2+1, 14+12+11+7+5+3+1, 14+12+11+9+1, 14+12+11+9+3+1, 14+12+11+9+5+1, 14+12+11+9+5+2+1, 14+12+11+9+5+3+1, 14+12+11+9+7+1, 14+12+11+9+7+3+1, 14+12+11+9+7+5+1, 14+12+11+9+7+5+2+1, 14+12+11+9+7+5+3+1, 15+1, 15+3+1, 15+5+1, 15+5+2+1, 15+5+3+1, 15+7+1, 15+7+3+1, 15+7+5+1, 15+7+5+2+1, 15+7+5+3+1, 15+9+1, 15+9+3+1, 15+9+5+1, 15+9+5+2+1, 15+9+5+3+1, 15+9+7+1, 15+9+7+3+1, 15+9+7+5+1, 15+9+7+5+2+1, 15+9+7+5+3+1, 15+11+1, 15+11+3+1, 15+11+5+1, 15+11+5+2+1, 15+11+5+3+1, 15+11+7+1, 15+11+7+3+1, 15+11+7+5+1, 15+11+7+5+2+1, 15+11+7+5+3+1, 15+11+9+1, 15+11+9+3+1, 15+11+9+5+1, 15+11+9+5+2+1, 15+11+9+5+3+1, 15+11+9+7+1, 15+11+9+7+3+1, 15+11+9+7+5+1, 15+11+9+7+5+2+1, 15+11+9+7+5+3+1, 15+14+12+1, 15+14+12+3+1, 15+14+12+5+1, 15+14+12+5+2+1, 15+14+12+5+3+1, 15+14+12+7+1, 15+14+12+7+3+1, 15+14+12+7+5+1, 15+14+12+7+5+2+1, 15+14+12+7+5+3+1, 15+14+12+9+1, 15+14+12+9+3+1, 15+14+12+9+5+1, 15+14+12+9+5+2+1, 15+14+12+9+5+3+1, 15+14+12+9+7+1, 15+14+12+9+7+3+1, 15+14+12+9+7+5+1, 15+14+12+9+7+5+2+1, 15+14+12+9+7+5+3+1, 15+14+12+11+1, 15+14+12+11+3+1, 15+14+12+11+5+1, 15+14+12+11+5+2+1, 15+14+12+11+5+3+1, 15+14+12+11+7+1, 15+14+12+11+7+3+1, 15+14+12+11+7+5+1, 15+14+12+11+7+5+2+1, 15+14+12+11+7+5+3+1, 15+14+12+11+9+1, 15+14+12+11+9+3+1, 15+14+12+11+9+5+1, 15+14+12+11+9+5+2+1, 15+14+12+11+9+5+3+1, 15+14+12+11+9+7+1, 15+14+12+11+9+7+3+1, 15+14+12+11+9+7+5+1, 15+14+12+11+9+7+5+2+1, 15+14+12+11+9+7+5+3+1, 16+1, 16+3+1, 16+5+1, 16+5+2+1, 16+5+3+1, 16+7+1, 16+7+3+1, 16+7+5+1, 16+7+5+2+1, 16+7+5+3+1, 16+9+1, 16+9+3+1, 16+9+5+1, 16+9+5+2+1, 16+9+5+3+1, 16+9+7+1, 16+9+7+3+1, 16+9+7+5+1, 16+9+7+5+2+1, 16+9+7+5+3+1, 16+11+1, 16+11+3+1, 16+11+5+1, 16+11+5+2+1, 16+11+5+3+1, 16+11+7+1, 16+11+7+3+1, 16+11+7+5+1, 16+11+7+5+2+1, 16+11+7+5+3+1, 16+11+9+1, 16+11+9+3+1, 16+11+9+5+1, 16+11+9+5+2+1, 16+11+9+5+3+1, 16+11+9+7+1, 16+11+9+7+3+1, 16+11+9+7+5+1, 16+11+9+7+5+2+1, 16+11+9+7+5+3+1, 16+14+12+1, 16+14+12+3+1, 16+14+12+5+1, 16+14+12+5+2+1, 16+14+12+5+3+1, 16+14+12+7+1, 16+14+12+7+3+1, 16+14+12+7+5+1, 16+14+12+7+5+2+1, 16+14+12+7+5+3+1, 16+14+12+9+1, 16+14+12+9+3+1, 16+14+12+9+5+1, 16+14+12+9+5+2+1, 16+14+12+9+5+3+1, 16+14+12+9+7+1, 16+14+12+9+7+3+1, 16+14+12+9+7+5+1, 16+14+12+9+7+5+2+1, 16+14+12+9+7+5+3+1, 16+14+12+11+1, 16+14+12+11+3+1, 16+14+12+11+5+1, 16+14+12+11+5+2+1, 16+14+12+11+5+3+1, 16+14+12+11+7+1, 16+14+12+11+7+3+1, 16+14+12+11+7+5+1, 16+14+12+11+7+5+2+1, 16+14+12+11+7+5+3+1, 16+14+12+11+9+1, 16+14+12+11+9+3+1, 16+14+12+11+9+5+1, 16+14+12+11+9+5+2+1, 16+14+12+11+9+5+3+1, 16+14+12+11+9+7+1, 16+14+12+11+9+7+3+1, 16+14+12+11+9+7+5+1, 16+14+12+11+9+7+5+2+1, 16+14+12+11+9+7+5+3+1, 16+15+1, 16+15+3+1, 16+15+5+1, 16+15+5+2+1, 16+15+5+3+1, 16+15+7+1, 16+15+7+3+1, 16+15+7+5+1, 16+15+7+5+2+1, 16+15+7+5+3+1, 16+15+9+1, 16+15+9+3+1, 16+15+9+5+1, 16+15+9+5+2+1, 16+15+9+5+3+1, 16+15+9+7+1, 16+15+9+7+3+1, 16+15+9+7+5+1, 16+15+9+7+5+2+1, 16+15+9+7+5+3+1, 16+15+11+1, 16+15+11+3+1, 16+15+11+5+1, 16+15+11+5+2+1, 16+15+11+5+3+1, 16+15+11+7+1, 16+15+11+7+3+1, 16+15+11+7+5+1, 16+15+11+7+5+2+1, 16+15+11+7+5+3+1, 16+15+11+9+1, 16+15+11+9+3+1, 16+15+11+9+5+1, 16+15+11+9+5+2+1, 16+15+11+9+5+3+1, 16+15+11+9+7+1, 16+15+11+9+7+3+1, 16+15+11+9+7+5+1, 16+15+11+9+7+5+2+1, 16+15+11+9+7+5+3+1, 16+15+14+12+1, 16+15+14+12+3+1, 16+15+14+12+5+1, 16+15+14+12+5+2+1, 16+15+14+12+5+3+1, 16+15+14+12+7+1, 16+15+14+12+7+3+1, 16+15+14+12+7+5+1, 16+15+14+12+7+5+2+1, 16+15+14+12+7+5+3+1, 16+15+14+12+9+1, 16+15+14+12+9+3+1, 16+15+14+12+9+5+1, 16+15+14+12+9+5+2+1, 16+15+14+12+9+5+3+1, 16+15+14+12+9+7+1, 16+15+14+12+9+7+3+1, 16+15+14+12+9+7+5+1, 16+15+14+12+9+7+5+2+1, 16+15+14+12+9+7+5+3+1, 16+15+14+12+11+1, 16+15+14+12+11+3+1, 16+15+14+12+11+5+1, 16+15+14+12+11+5+2+1, 16+15+14+12+11+5+3+1, 16+15+14+12+11+7+1, 16+15+14+12+11+7+3+1, 16+15+14+12+11+7+5+1, 16+15+14+12+11+7+5+2+1, 16+15+14+12+11+7+5+3+1, 16+15+14+12+11+9+1, 16+15+14+12+11+9+3+1, 16+15+14+12+11+9+5+1, 16+15+14+12+11+9+5+2+1, 16+15+14+12+11+9+5+3+1, 16+15+14+12+11+9+7+1, 16+15+14+12+11+9+7+3+1, 16+15+14+12+11+9+7+5+1, 16+15+14+12+11+9+7+5+2+1, 16+15+14+12+11+9+7+5+3+1, 17+1, 17+3+1, 17+5+1, 17+5+2+1, 17+5+3+1, 17+7+1, 17+7+3+1, 17+7+5+1, 17+7+5+2+1, 17+7+5+3+1, 17+9+1, 17+9+3+1, 17+9+5+1, 17+9+5+2+1, 17+9+5+3+1, 17+9+7+1, 17+9+7+3+1, 17+9+7+5+1, 17+9+7+5+2+1, 17+9+7+5+3+1, 17+11+1, 17+11+3+1, 17+11+5+1, 17+11+5+2+1, 17+11+5+3+1, 17+11+7+1, 17+11+7+3+1, 17+11+7+5+1, 17+11+7+5+2+1, 17+11+7+5+3+1, 17+11+9+1, 17+11+9+3+1, 17+11+9+5+1, 17+11+9+5+2+1, 17+11+9+5+3+1, 17+11+9+7+1, 17+11+9+7+3+1, 17+11+9+7+5+1, 17+11+9+7+5+2+1, 17+11+9+7+5+3+1, 17+14+12+1, 17+14+12+3+1, 17+14+12+5+1, 17+14+12+5+2+1, 17+14+12+5+3+1, 17+14+12+7+1, 17+14+12+7+3+1, 17+14+12+7+5+1, 17+14+12+7+5+2+1, 17+14+12+7+5+3+1, 17+14+12+9+1, 17+14+12+9+3+1, 17+14+12+9+5+1, 17+14+12+9+5+2+1, 17+14+12+9+5+3+1, 17+14+12+9+7+1, 17+14+12+9+7+3+1, 17+14+12+9+7+5+1, 17+14+12+9+7+5+2+1, 17+14+12+9+7+5+3+1, 17+14+12+11+1, 17+14+12+11+3+1, 17+14+12+11+5+1, 17+14+12+11+5+2+1, 17+14+12+11+5+3+1, 17+14+12+11+7+1, 17+14+12+11+7+3+1, 17+14+12+11+7+5+1, 17+14+12+11+7+5+2+1, 17+14+12+11+7+5+3+1, 17+14+12+11+9+1, 17+14+12+11+9+3+1, 17+14+12+11+9+5+1, 17+14+12+11+9+5+2+1, 17+14+12+11+9+5+3+1, 17+14+12+11+9+7+1, 17+14+12+11+9+7+3+1, 17+14+12+11+9+7+5+1, 17+14+12+11+9+7+5+2+1, 17+14+12+11+9+7+5+3+1, 18+16+1, 18+16+3+1, 18+16+5+1, 18+16+5+2+1, 18+16+5+3+1, 18+16+7+1, 18+16+7+3+1, 18+16+7+5+1, 18+16+7+5+2+1, 18+16+7+5+3+1, 18+16+9+1, 18+16+9+3+1, 18+16+9+5+1, 18+16+9+5+2+1, 18+16+9+5+3+1, 18+16+9+7+1, 18+16+9+7+3+1, 18+16+9+7+5+1, 18+16+9+7+5+2+1, 18+16+9+7+5+3+1, 18+16+11+1, 18+16+11+3+1, 18+16+11+5+1, 18+16+11+5+2+1, 18+16+11+5+3+1, 18+16+11+7+1, 18+16+11+7+3+1, 18+16+11+7+5+1, 18+16+11+7+5+2+1, 18+16+11+7+5+3+1, 18+16+11+9+1, 18+16+11+9+3+1, 18+16+11+9+5+1, 18+16+11+9+5+2+1, 18+16+11+9+5+3+1, 18+16+11+9+7+1, 18+16+11+9+7+3+1, 18+16+11+9+7+5+1, 18+16+11+9+7+5+2+1, 18+16+11+9+7+5+3+1, 18+16+14+12+1, 18+16+14+12+3+1, 18+16+14+12+5+1, 18+16+14+12+5+2+1, 18+16+14+12+5+3+1, 18+16+14+12+7+1, 18+16+14+12+7+3+1, 18+16+14+12+7+5+1, 18+16+14+12+7+5+2+1, 18+16+14+12+7+5+3+1, 18+16+14+12+9+1, 18+16+14+12+9+3+1, 18+16+14+12+9+5+1, 18+16+14+12+9+5+2+1, 18+16+14+12+9+5+3+1, 18+16+14+12+9+7+1, 18+16+14+12+9+7+3+1, 18+16+14+12+9+7+5+1, 18+16+14+12+9+7+5+2+1, 18+16+14+12+9+7+5+3+1, 18+16+14+12+11+1, 18+16+14+12+11+3+1, 18+16+14+12+11+5+1, 18+16+14+12+11+5+2+1, 18+16+14+12+11+5+3+1, 18+16+14+12+11+7+1, 18+16+14+12+11+7+3+1, 18+16+14+12+11+7+5+1, 18+16+14+12+11+7+5+2+1, 18+16+14+12+11+7+5+3+1, 18+16+14+12+11+9+1, 18+16+14+12+11+9+3+1, 18+16+14+12+11+9+5+1, 18+16+14+12+11+9+5+2+1, 18+16+14+12+11+9+5+3+1, 18+16+14+12+11+9+7+1, 18+16+14+12+11+9+7+3+1, 18+16+14+12+11+9+7+5+1, 18+16+14+12+11+9+7+5+2+1, 18+16+14+12+11+9+7+5+3+1, 18+16+15+1, 18+16+15+3+1, 18+16+15+5+1, 18+16+15+5+2+1, 18+16+15+5+3+1, 18+16+15+7+1, 18+16+15+7+3+1, 18+16+15+7+5+1, 18+16+15+7+5+2+1, 18+16+15+7+5+3+1, 18+16+15+9+1, 18+16+15+9+3+1, 18+16+15+9+5+1, 18+16+15+9+5+2+1, 18+16+15+9+5+3+1, 18+16+15+9+7+1, 18+16+15+9+7+3+1, 18+16+15+9+7+5+1, 18+16+15+9+7+5+2+1, 18+16+15+9+7+5+3+1, 18+16+15+11+1, 18+16+15+11+3+1, 18+16+15+11+5+1, 18+16+15+11+5+2+1, 18+16+15+11+5+3+1, 18+16+15+11+7+1, 18+16+15+11+7+3+1, 18+16+15+11+7+5+1, 18+16+15+11+7+5+2+1, 18+16+15+11+7+5+3+1, 18+16+15+11+9+1, 18+16+15+11+9+3+1, 18+16+15+11+9+5+1, 18+16+15+11+9+5+2+1, 18+16+15+11+9+5+3+1, 18+16+15+11+9+7+1, 18+16+15+11+9+7+3+1, 18+16+15+11+9+7+5+1, 18+16+15+11+9+7+5+2+1, 18+16+15+11+9+7+5+3+1, 18+16+15+14+12+1, 18+16+15+14+12+3+1, 18+16+15+14+12+5+1, 18+16+15+14+12+5+2+1, 18+16+15+14+12+5+3+1, 18+16+15+14+12+7+1, 18+16+15+14+12+7+3+1, 18+16+15+14+12+7+5+1, 18+16+15+14+12+7+5+2+1, 18+16+15+14+12+7+5+3+1, 18+16+15+14+12+9+1, 18+16+15+14+12+9+3+1, 18+16+15+14+12+9+5+1, 18+16+15+14+12+9+5+2+1, 18+16+15+14+12+9+5+3+1, 18+16+15+14+12+9+7+1, 18+16+15+14+12+9+7+3+1, 18+16+15+14+12+9+7+5+1, 18+16+15+14+12+9+7+5+2+1, 18+16+15+14+12+9+7+5+3+1, 18+16+15+14+12+11+1, 18+16+15+14+12+11+3+1, 18+16+15+14+12+11+5+1, 18+16+15+14+12+11+5+2+1, 18+16+15+14+12+11+5+3+1, 18+16+15+14+12+11+7+1, 18+16+15+14+12+11+7+3+1, 18+16+15+14+12+11+7+5+1, 18+16+15+14+12+11+7+5+2+1, 18+16+15+14+12+11+7+5+3+1, 18+16+15+14+12+11+9+1, 18+16+15+14+12+11+9+3+1, 18+16+15+14+12+11+9+5+1, 18+16+15+14+12+11+9+5+2+1, 18+16+15+14+12+11+9+5+3+1, 18+16+15+14+12+11+9+7+1, 18+16+15+14+12+11+9+7+3+1, 18+16+15+14+12+11+9+7+5+1, 18+16+15+14+12+11+9+7+5+2+1, 18+16+15+14+12+11+9+7+5+3+1, 19+16+1, 19+16+3+1, 19+16+5+1, 19+16+5+2+1, 19+16+5+3+1, 19+16+7+1, 19+16+7+3+1, 19+16+7+5+1, 19+16+7+5+2+1, 19+16+7+5+3+1, 19+16+9+1, 19+16+9+3+1, 19+16+9+5+1, 19+16+9+5+2+1, 19+16+9+5+3+1, 19+16+9+7+1, 19+16+9+7+3+1, 19+16+9+7+5+1, 19+16+9+7+5+2+1, 19+16+9+7+5+3+1, 19+16+11+1, 19+16+11+3+1, 19+16+11+5+1, 19+16+11+5+2+1, 19+16+11+5+3+1, 19+16+11+7+1, 19+16+11+7+3+1, 19+16+11+7+5+1, 19+16+11+7+5+2+1, 19+16+11+7+5+3+1, 19+16+11+9+1, 19+16+11+9+3+1, 19+16+11+9+5+1, 19+16+11+9+5+2+1, 19+16+11+9+5+3+1, 19+16+11+9+7+1, 19+16+11+9+7+3+1, 19+16+11+9+7+5+1, 19+16+11+9+7+5+2+1, 19+16+11+9+7+5+3+1, 19+16+14+12+1, 19+16+14+12+3+1, 19+16+14+12+5+1, 19+16+14+12+5+2+1, 19+16+14+12+5+3+1, 19+16+14+12+7+1, 19+16+14+12+7+3+1, 19+16+14+12+7+5+1, 19+16+14+12+7+5+2+1, 19+16+14+12+7+5+3+1, 19+16+14+12+9+1, 19+16+14+12+9+3+1, 19+16+14+12+9+5+1, 19+16+14+12+9+5+2+1, 19+16+14+12+9+5+3+1, 19+16+14+12+9+7+1, 19+16+14+12+9+7+3+1, 19+16+14+12+9+7+5+1, 19+16+14+12+9+7+5+2+1, 19+16+14+12+9+7+5+3+1, 19+16+14+12+11+1, 19+16+14+12+11+3+1, 19+16+14+12+11+5+1, 19+16+14+12+11+5+2+1, 19+16+14+12+11+5+3+1, 19+16+14+12+11+7+1, 19+16+14+12+11+7+3+1, 19+16+14+12+11+7+5+1, 19+16+14+12+11+7+5+2+1, 19+16+14+12+11+7+5+3+1, 19+16+14+12+11+9+1, 19+16+14+12+11+9+3+1, 19+16+14+12+11+9+5+1, 19+16+14+12+11+9+5+2+1, 19+16+14+12+11+9+5+3+1, 19+16+14+12+11+9+7+1, 19+16+14+12+11+9+7+3+1, 19+16+14+12+11+9+7+5+1, 19+16+14+12+11+9+7+5+2+1, 19+16+14+12+11+9+7+5+3+1, 19+16+15+1, 19+16+15+3+1, 19+16+15+5+1, 19+16+15+5+2+1, 19+16+15+5+3+1, 19+16+15+7+1, 19+16+15+7+3+1, 19+16+15+7+5+1, 19+16+15+7+5+2+1, 19+16+15+7+5+3+1, 19+16+15+9+1, 19+16+15+9+3+1, 19+16+15+9+5+1, 19+16+15+9+5+2+1, 19+16+15+9+5+3+1, 19+16+15+9+7+1, 19+16+15+9+7+3+1, 19+16+15+9+7+5+1, 19+16+15+9+7+5+2+1, 19+16+15+9+7+5+3+1, 19+16+15+11+1, 19+16+15+11+3+1, 19+16+15+11+5+1, 19+16+15+11+5+2+1, 19+16+15+11+5+3+1, 19+16+15+11+7+1, 19+16+15+11+7+3+1, 19+16+15+11+7+5+1, 19+16+15+11+7+5+2+1, 19+16+15+11+7+5+3+1, 19+16+15+11+9+1, 19+16+15+11+9+3+1, 19+16+15+11+9+5+1, 19+16+15+11+9+5+2+1, 19+16+15+11+9+5+3+1, 19+16+15+11+9+7+1, 19+16+15+11+9+7+3+1, 19+16+15+11+9+7+5+1, 19+16+15+11+9+7+5+2+1, 19+16+15+11+9+7+5+3+1, 19+16+15+14+12+1, 19+16+15+14+12+3+1, 19+16+15+14+12+5+1, 19+16+15+14+12+5+2+1, 19+16+15+14+12+5+3+1, 19+16+15+14+12+7+1, 19+16+15+14+12+7+3+1, 19+16+15+14+12+7+5+1, 19+16+15+14+12+7+5+2+1, 19+16+15+14+12+7+5+3+1, 19+16+15+14+12+9+1, 19+16+15+14+12+9+5+1, 19+16+15+14+12+9+5+2+1, 19+16+15+14+12+9+5+3+1, 19+16+15+14+12+9+7+1, 19+16+15+14+12+9+7+3+1, 19+16+15+14+12+9+7+5+1, 19+16+15+14+12+9+7+5+2+1, 19+16+15+14+12+9+7+5+3+1, 19+16+15+14+12+11+1, 19+16+15+14+12+11+3+1, 19+16+15+14+12+11+5+1, 19+16+15+14+12+11+5+2+1, 19+16+15+14+12+11+5+3+1, 19+16+15+14+12+11+7+1, 19+16+15+14+12+11+7+3+1, 19+16+15+14+12+11+7+5+1, 19+16+15+14+12+11+7+5+2+1, 19+16+15+14+12+11+7+5+3+1, 19+16+15+14+12+11+9+1, 19+16+15+14+12+11+9+3+1, 19+16+15+14+12+11+9+5+1, 19+16+15+14+12+11+9+5+2+1, 19+16+15+14+12+11+9+5+3+1, 19+16+15+14+12+11+9+7+1, 19+16+15+14+12+11+9+7+3+1, 19+16+15+14+12+11+9+7+5+1, 19+16+15+14+12+11+9+7+5+2+1, 19+16+15+14+12+11+9+7+5+3+1, 20+1, 20+3+1, 20+5+1, 20+5+2+1, 20+5+3+1, 20+7+1, 20+7+3+1, 20+7+5+1, 20+7+5+2+1, 20+7+5+3+1, 20+9+1, 20+9+3+1, 20+9+5+1, 20+9+5+2+1, 20+9+5+3+1, 20+9+7+1, 20+9+7+3+1, 20+9+7+5+1, 20+9+7+5+2+1, 20+9+7+5+3+1, 20+11+1, 20+11+3+1, 20+11+5+1, 20+11+5+2+1, 20+11+5+3+1, 20+11+7+1, 20+11+7+3+1, 20+11+7+5+1, 20+11+7+5+2+1, 20+11+7+5+3+1, 20+11+9+1, 20+11+9+3+1, 20+11+9+5+1, 20+11+9+5+2+1, 20+11+9+5+3+1, 20+11+9+7+1, 20+11+9+7+3+1, 20+11+9+7+5+1, 20+11+9+7+5+2+1, 20+11+9+7+5+3+1, 20+14+12+1, 20+14+12+3+1, 20+14+12+5+1, 20+14+12+5+2+1, 20+14+12+5+3+1, 20+14+12+7+1, 20+14+12+7+3+1, 20+14+12+7+5+1, 20+14+12+7+5+2+1, 20+14+12+7+5+3+1, 20+14+12+9+1, 20+14+12+9+3+1, 20+14+12+9+5+1, 20+14+12+9+5+2+1, 20+14+12+9+5+3+1, 20+14+12+9+7+1, 20+14+12+9+7+3+1, 20+14+12+9+7+5+1, 20+14+12+9+7+5+2+1, 20+14+12+9+7+5+3+1, 20+14+12+11+1, 20+14+12+11+3+1, 20+14+12+11+5+1, 20+14+12+11+5+2+1, 20+14+12+11+5+3+1, 20+14+12+11+7+1, 20+14+12+11+7+3+1, 20+14+12+11+7+5+1, 20+14+12+11+7+5+2+1, 20+14+12+11+7+5+3+1, 20+14+12+11+9+1, 20+14+12+11+9+3+1, 20+14+12+11+9+5+1, 20+14+12+11+9+5+2+1, 20+14+12+11+9+5+3+1, 20+14+12+11+9+7+1, 20+14+12+11+9+7+3+1, 20+14+12+11+9+7+5+1, 20+14+12+11+9+7+5+2+1, 20+14+12+11+9+7+5+3+1, 20+15+1, 20+15+3+1, 20+15+5+1, 20+15+5+2+1, 20+15+5+3+1, 20+15+7+1, 20+15+7+3+1, 20+15+7+5+1, 20+15+7+5+2+1, 20+15+7+5+3+1, 20+15+9+1, 20+15+9+3+1, 20+15+9+5+1, 20+15+9+5+2+1, 20+15+9+5+3+1, 20+15+9+7+1, 20+15+9+7+3+1, 20+15+9+7+5+1, 20+15+9+7+5+2+1, 20+15+9+7+5+3+1, 20+15+11+1, 20+15+11+3+1, 20+15+11+5+1, 20+15+11+5+2+1, 20+15+11+5+3+1, 20+15+11+7+1, 20+15+11+7+3+1, 20+15+11+7+5+1, 20+15+11+7+5+2+1, 20+15+11+7+5+3+1, 20+15+11+9+1, 20+15+11+9+3+1, 20+15+11+9+5+1, 20+15+11+9+5+2+1, 20+15+11+9+5+3+1, 20+15+11+9+7+1, 20+15+11+9+7+3+1, 20+15+11+9+7+5+1, 20+15+11+9+7+5+2+1, 20+15+11+9+7+5+3+1, 20+15+14+12+1, 20+15+14+12+3+1, 20+15+14+12+5+1, 20+15+14+12+5+2+1, 20+15+14+12+5+3+1, 20+15+14+12+7+1, 20+15+14+12+7+3+1, 20+15+14+12+7+5+1, 20+15+14+12+7+5+2+1, 20+15+14+12+7+5+3+1, 20+15+14+12+9+1, 20+15+14+12+9+3+1, 20+15+14+12+9+5+1, 20+15+14+12+9+5+2+1, 20+15+14+12+9+5+3+1, 20+15+14+12+9+7+1, 20+15+14+12+9+7+3+1, 20+15+14+12+9+7+5+1, 20+15+14+12+9+7+5+2+1, 20+15+14+12+9+7+5+3+1, 20+15+14+12+11+1, 20+15+14+12+11+3+1, 20+15+14+12+11+5+1, 20+15+14+12+11+5+2+1, 20+15+14+12+11+5+3+1, 20+15+14+12+11+7+1, 20+15+14+12+11+7+3+1, 20+15+14+12+11+7+5+1, 20+15+14+12+11+7+5+2+1, 20+15+14+12+11+7+5+3+1, 20+15+14+12+11+9+1, 20+15+14+12+11+9+3+1, 20+15+14+12+11+9+5+1, 20+15+14+12+11+9+5+2+1, 20+15+14+12+11+9+5+3+1, 20+15+14+12+11+9+7+1, 20+15+14+12+11+9+7+3+1, 20+15+14+12+11+9+7+5+1, 20+15+14+12+11+9+7+5+2+1, 20+15+14+12+11+9+7+5+3+1, 20+16+1, 20+16+3+1, 20+16+5+1, 20+16+5+2+1, 20+16+5+3+1, 20+16+7+1, 20+16+7+3+1, 20+16+7+5+1, 20+16+7+5+2+1, 20+16+7+5+3+1, 20+16+9+1, 20+16+9+3+1, 20+16+9+5+1, 20+16+9+5+2+1, 20+16+9+5+3+1, 20+16+9+7+1, 20+16+9+7+3+1, 20+16+9+7+5+1, 20+16+9+7+5+2+1, 20+16+9+7+5+3+1, 20+16+11+1, 20+16+11+3+1, 20+16+11+5+1, 20+16+11+5+2+1, 20+16+11+5+3+1, 20+16+11+7+1, 20+16+11+7+3+1, 20+16+11+7+5+1, 20+16+11+7+5+2+1, 20+16+11+7+5+3+1, 20+16+11+9+1, 20+16+11+9+3+1, 20+16+11+9+5+1, 20+16+11+9+5+2+1, 20+16+11+9+5+3+1, 20+16+11+9+7+1, 20+16+11+9+7+3+1, 20+16+11+9+7+5+1, 20+16+11+9+7+5+2+1, 20+16+11+9+7+5+3+1, 20+16+14+12+1, 20+16+14+12+3+1, 20+16+14+12+5+1, 20+16+14+12+5+2+1, 20+16+14+12+5+3+1, 20+16+14+12+7+1, 20+16+14+12+7+3+1, 20+16+14+12+7+5+1, 20+16+14+12+7+5+2+1, 20+16+14+12+7+5+3+1, 20+16+14+12+9+1, 20+16+14+12+9+3+1, 20+16+14+12+9+5+1, 20+16+14+12+9+5+2+1, 20+16+14+12+9+5+3+1, 20+16+14+12+9+7+1, 20+16+14+12+9+7+3+1, 20+16+14+12+9+7+5+1, 20+16+14+12+9+7+5+2+1, 20+16+14+12+9+7+5+3+1, 20+16+14+12+11+1, 20+16+14+12+11+3+1, 20+16+14+12+11+5+1, 20+16+14+12+11+5+2+1, 20+16+14+12+11+5+3+1, 20+16+14+12+11+7+1, 20+16+14+12+11+7+3+1, 20+16+14+12+11+7+5+1, 20+16+14+12+11+7+5+2+1, 20+16+14+12+11+7+5+3+1, 20+16+14+12+11+9+1, 20+16+14+12+11+9+3+1, 20+16+14+12+11+9+5+1, 20+16+14+12+11+9+5+2+1, 20+16+14+12+11+9+5+3+1, 20+16+14+12+11+9+7+1, 20+16+14+12+11+9+7+3+1, 20+16+14+12+11+9+7+5+1, 20+16+14+12+11+9+7+5+2+1, 20+16+14+12+11+9+7+5+3+1, 20+16+15+1, 20+16+15+3+1, 20+16+15+5+1, 20+16+15+5+2+1, 20+16+15+5+3+1, 20+16+15+7+1, 20+16+15+7+3+1, 20+16+15+7+5+1, 20+16+15+7+5+2+1, 20+16+15+7+5+3+1, 20+16+15+9+1, 20+16+15+9+3+1, 20+16+15+9+5+1, 20+16+15+9+5+2+1, 20+16+15+9+5+3+1, 20+16+15+9+7+1, 20+16+15+9+7+3+1, 20+16+15+9+7+5+1, 20+16+15+9+7+5+2+1, 20+16+15+9+7+5+3+1, 20+16+15+11+1, 20+16+15+11+3+1, 20+16+15+11+5+1, 20+16+15+11+5+2+1, 20+16+15+11+5+3+1, 20+16+15+11+7+1, 20+16+15+11+7+3+1, 20+16+15+11+7+5+1, 20+16+15+11+7+5+2+1, 20+16+15+11+7+5+3+1, 20+16+15+11+9+1, 20+16+15+11+9+3+1, 20+16+15+11+9+5+1, 20+16+15+11+9+5+2+1, 20+16+15+11+9+5+3+1, 20+16+15+11+9+7+1, 20+16+15+11+9+7+3+1, 20+16+15+11+9+7+5+1, 20+16+15+11+9+7+5+2+1, 20+16+15+11+9+7+5+3+1, 20+16+15+14+12+1, 20+16+15+14+12+3+1, 20+16+15+14+12+5+1, 20+16+15+14+12+5+2+1, 20+16+15+14+12+5+3+1, 20+16+15+14+12+7+1, 20+16+15+14+12+7+3+1, 20+16+15+14+12+7+5+1, 20+16+15+14+12+7+5+2+1, 20+16+15+14+12+7+5+3+1, 20+16+15+14+12+9+1, 20+16+15+14+12+9+3+1, 20+16+15+14+12+9+5+1, 20+16+15+14+12+9+5+2+1, 20+16+15+14+12+9+5+3+1, 20+16+15+14+12+9+7+1, 20+16+15+14+12+9+7+3+1, 20+16+15+14+12+9+7+5+1, 20+16+15+14+12+9+7+5+2+1, 20+16+15+14+12+9+7+5+3+1, 20+16+15+14+12+11+1, 20+16+15+14+12+11+3+1, 20+16+15+14+12+11+5+1, 20+16+15+14+12+11+5+2+1, 20+16+15+14+12+11+5+3+1, 20+16+15+14+12+11+7+1, 20+16+15+14+12+11+7+3+1, 20+16+15+14+12+11+7+5+1, 20+16+15+14+12+11+7+5+2+1, 20+16+15+14+12+11+7+5+3+1, 20+16+15+14+12+11+9+1, 20+16+15+14+12+11+9+3+1, 20+16+15+14+12+11+9+5+1, 20+16+15+14+12+11+9+5+2+1, 20+16+15+14+12+11+9+5+3+1, 20+16+15+14+12+11+9+7+1, 20+16+15+14+12+11+9+7+3+1, 20+16+15+14+12+11+9+7+5+1, 20+16+15+14+12+11+9+7+5+2+1, 20+16+15+14+12+11+9+7+5+3+1, 20+19+16+1, 20+19+16+3+1, 20+19+16+5+1, 20+19+16+5+2+1, 20+19+16+5+3+1, 20+19+16+7+1, 20+19+16+7+3+1, 20+19+16+7+5+1, 20+19+16+7+5+2+1, 20+19+16+7+5+3+1, 20+19+16+9+1, 20+19+16+9+3+1, 20+19+16+9+5+1, 20+19+16+9+5+2+1, 20+19+16+9+5+3+1, 20+19+16+9+7+1, 20+19+16+9+7+3+1, 20+19+16+9+7+5+1, 20+19+16+9+7+5+2+1, 20+19+16+9+7+5+3+1, 20+19+16+11+1, 20+19+16+11+3+1, 20+19+16+11+5+1, 20+19+16+11+5+2+1, 20+19+16+11+5+3+1, 20+19+16+11+7+1, 20+19+16+11+7+3+1, 20+19+16+11+7+5+1, 20+19+16+11+7+5+2+1, 20+19+16+11+7+5+3+1, 20+19+16+11+9+1, 20+19+16+11+9+3+1, 20+19+16+11+9+5+1, 20+19+16+11+9+5+2+1, 20+19+16+11+9+5+3+1, 20+19+16+11+9+7+1, 20+19+16+11+9+7+3+1, 20+19+16+11+9+7+5+1, 20+19+16+11+9+7+5+2+1, 20+19+16+11+9+7+5+3+1, 20+19+16+14+12+1, 20+19+16+14+12+3+1, 20+19+16+14+12+5+1, 20+19+16+14+12+5+2+1, 20+19+16+14+12+5+3+1, 20+19+16+14+12+7+1, 20+19+16+14+12+7+3+1, 20+19+16+14+12+7+5+1, 20+19+16+14+12+7+5+2+1, 20+19+16+14+12+7+5+3+1, 20+19+16+14+12+9+1, 20+19+16+14+12+9+3+1, 20+19+16+14+12+9+5+1, 20+19+16+14+12+9+5+2+1, 20+19+16+14+12+9+5+3+1, 20+19+16+14+12+9+7+1, 20+19+16+14+12+9+7+3+1, 20+19+16+14+

12+9+7+5+1, 20+19+16+14+12+9+7+5+2+1, 20+19+16+14+12+9+7+5+3+1, 20+19+16+14+12+11+1, 20+19+16+14+12+11+3+1, 20+19+16+14+12+11+5+1, 20+19+16+14+12+11+5+2+1, 20+19+16+14+12+11+5+3+1, 20+19+16+14+12+11+7+1, 20+19+16+14+12+11+7+3+1, 20+19+16+14+12+11+7+5+1, 20+19+16+14+12+11+7+5+2+1, 20+19+16+14+12+11+7+5+3+1, 20+19+16+14+12+11+9+1, 20+19+16+14+12+11+9+3+1, 20+19+16+14+12+11+9+5+1, 20+19+16+14+12+11+9+5+2+1, 20+19+16+14+12+11+9+5+3+1, 20+19+16+14+12+11+9+7+1, 20+19+16+14+12+11+9+7+3+1, 20+19+16+14+12+11+9+7+5+1, 20+19+16+14+12+11+9+7+5+2+1, 20+19+16+14+12+11+9+7+5+3+1, 20+19+16+15+1, 20+19+16+15+3+1, 20+19+16+15+5+1, 20+19+16+15+5+2+1, 20+19+16+15+5+3+1, 20+19+16+15+7+1, 20+19+16+15+7+3+1, 20+19+16+15+7+5+1, 20+19+16+15+7+5+2+1, 20+19+16+15+7+5+3+1, 20+19+16+15+9+1, 20+19+16+15+9+3+1, 20+19+16+15+9+5+1, 20+19+16+15+9+5+2+1, 20+19+16+15+9+5+3+1, 20+19+16+15+9+7+1, 20+19+16+15+9+7+3+1, 20+19+16+15+9+7+5+1, 20+19+16+15+9+7+5+2+1, 20+19+16+15+9+7+5+3+1, 20+19+16+15+11+1, 20+19+16+15+11+3+1, 20+19+16+15+11+5+1, 20+19+16+15+11+5+2+1, 20+19+16+15+11+5+3+1, 20+19+16+15+11+7+1, 20+19+16+15+11+7+3+1, 20+19+16+15+11+7+5+1, 20+19+16+15+11+7+5+2+1, 20+19+16+15+11+7+5+3+1, 20+19+16+15+11+9+1, 20+19+16+15+11+9+3+1, 20+19+16+15+11+9+5+1, 20+19+16+15+11+9+5+2+1, 20+19+16+15+11+9+5+3+1, 20+19+16+15+11+9+7+1, 20+19+16+15+11+9+7+3+1, 20+19+16+15+11+9+7+5+1, 20+19+16+15+11+9+7+5+2+1, 20+19+16+15+11+9+7+5+3+1, 20+19+16+15+14+12+1, 20+19+16+15+14+12+3+1, 20+19+16+15+14+12+5+1, 20+19+16+15+14+12+5+2+1, 20+19+16+15+14+12+5+3+1, 20+19+16+15+14+12+7+1, 20+19+16+15+14+12+7+3+1, 20+19+16+15+14+12+7+5+1, 20+19+16+15+14+12+7+5+2+1, 20+19+16+15+14+12+7+5+3+1, 20+19+16+15+14+12+9+1, 20+19+16+15+14+12+9+3+1, 20+19+16+15+14+12+9+5+1, 20+19+16+15+14+12+9+5+2+1, 20+19+16+15+14+12+9+5+3+1, 20+19+16+15+14+12+9+7+1, 20+19+16+15+14+12+9+7+3+1, 20+19+16+15+14+12+9+7+5+1, 20+19+16+15+14+12+9+7+5+2+1, 20+19+16+15+14+12+9+7+5+3+1, 20+19+16+15+14+12+11+1, 20+19+16+15+14+12+11+3+1, 20+19+16+15+14+12+11+5+1, 20+19+16+15+14+12+11+5+2+1, 20+19+16+15+14+12+11+5+3+1, 20+19+16+15+14+12+11+7+1, 20+19+16+15+14+12+11+7+3+1, 20+19+16+15+14+12+11+7+5+1, 20+19+16+15+14+12+11+7+5+2+1, 20+19+16+15+14+12+11+7+5+3+1, 20+19+16+15+14+12+11+9+1, 20+19+16+15+14+12+11+9+3+1, 20+19+16+15+14+12+11+9+5+1, 20+19+16+15+14+12+11+9+5+2+1, 20+19+16+15+14+12+11+9+5+3+1, 20+19+16+15+14+12+11+9+7+1, 20+19+16+15+14+12+11+9+7+3+1, 20+19+16+15+14+12+11+9+7+5+1, 20+19+16+15+14+12+11+9+7+5+2+1, 20+19+16+15+14+12+11+9+7+5+3+1, 21+1, 21+3+1, 21+5+1, 21+5+2+1, 21+5+3+1, 21+7+1, 21+7+3+1, 21+7+5+1, 21+7+5+2+1, 21+7+5+3+1, 21+9+1, 21+9+3+1, 21+9+5+1, 21+9+5+2+1, 21+9+5+3+1, 21+9+7+1, 21+9+7+3+1, 21+9+7+5+1, 21+9+7+5+2+1, 21+9+7+5+3+1, 21+11+1, 21+11+3+1, 21+11+5+1, 21+11+5+2+1, 21+11+5+3+1, 21+11+7+1, 21+11+7+3+1, 21+11+7+5+1, 21+11+7+5+2+1, 21+11+7+5+3+1, 21+11+9+1, 21+11+9+3+1, 21+11+9+5+1, 21+11+9+5+2+1, 21+11+9+5+3+1, 21+11+9+7+1, 21+11+9+7+3+1, 21+11+9+7+5+1, 21+11+9+7+5+2+1, 21+11+9+7+5+3+1, 21+14+12+1, 21+14+12+3+1, 21+14+12+5+1, 21+14+12+5+2+1, 21+14+12+5+3+1, 21+14+12+7+1, 21+14+12+7+3+1, 21+14+12+7+5+1, 21+14+12+7+5+2+1, 21+14+12+7+5+3+1, 21+14+12+9+1, 21+14+12+9+3+1, 21+14+12+9+5+1, 21+14+12+9+5+2+1, 21+14+12+9+5+3+1, 21+14+12+9+7+1, 21+14+12+9+7+3+1, 21+14+12+9+7+5+1, 21+14+12+9+7+5+2+1, 21+14+12+9+7+5+3+1, 21+14+12+11+1, 21+14+12+11+3+1, 21+14+12+11+5+1, 21+14+12+11+5+2+1, 21+14+12+11+5+3+1, 21+14+12+11+7+1, 21+14+12+11+7+3+1, 21+14+12+11+7+5+1, 21+14+12+11+7+5+2+1, 21+14+12+11+7+5+3+1, 21+14+12+11+9+1, 21+14+12+11+9+3+1, 21+14+12+11+9+5+1, 21+14+12+11+9+5+2+1, 21+14+12+11+9+5+3+1, 21+14+12+11+9+7+1, 21+14+12+11+9+7+3+1, 21+14+12+11+9+7+5+1, 21+14+12+11+9+7+5+2+1, 21+14+12+11+9+7+5+3+1, 21+15+1, 21+15+3+1, 21+15+5+1, 21+15+5+2+1, 21+15+5+3+1, 21+15+7+1, 21+15+7+3+1, 21+15+7+5+1, 21+15+7+5+2+1, 21+15+7+5+3+1, 21+15+9+1, 21+15+9+3+1, 21+15+9+5+1, 21+15+9+5+2+1, 21+15+9+5+3+1, 21+15+9+7+1, 21+15+9+7+3+1, 21+15+9+7+5+1, 21+15+9+7+5+2+1, 21+15+9+7+5+3+1, 21+15+11+1, 21+15+11+3+1, 21+15+11+5+1, 21+15+11+5+2+1, 21+15+11+5+3+1, 21+15+11+7+1, 21+15+11+7+3+1, 21+15+11+7+5+1, 21+15+11+7+5+2+1, 21+15+11+7+5+3+1, 21+15+11+9+1, 21+15+11+9+3+1, 21+15+11+9+5+1, 21+15+11+9+5+2+1, 21+15+11+9+5+3+1, 21+15+11+9+7+1, 21+15+11+9+7+3+1, 21+15+11+9+7+5+1, 21+15+11+9+7+5+2+1, 21+15+11+9+7+5+3+1, 21+15+14+12+1, 21+15+14+12+3+1, 21+15+14+12+5+1, 21+15+14+12+5+2+1, 21+15+14+12+5+3+1, 21+15+14+12+7+1, 21+15+14+12+7+3+1, 21+15+14+12+7+5+1, 21+15+14+12+7+5+2+1, 21+15+14+12+7+5+3+1, 21+15+14+12+9+1, 21+15+14+12+9+3+1, 21+15+14+12+9+5+1, 21+15+14+12+9+5+2+1, 21+15+14+12+9+5+3+1, 21+15+14+12+9+7+1, 21+15+14+12+9+7+3+1, 21+15+14+12+9+7+5+1, 21+15+14+12+9+7+5+2+1, 21+15+14+12+9+7+5+3+1, 21+15+14+12+11+1, 21+15+14+12+11+3+1, 21+15+14+12+11+5+1, 21+15+14+12+11+5+2+1, 21+15+14+12+11+5+3+1, 21+15+14+12+11+7+1, 21+15+14+12+11+7+3+1, 21+15+14+12+11+7+5+1, 21+15+14+12+11+7+5+2+1, 21+15+14+12+11+7+5+3+1, 21+15+14+12+11+9+1, 21+15+14+12+11+9+3+1, 21+15+14+12+11+9+5+1, 21+15+14+12+11+9+5+2+1, 21+15+14+12+11+9+5+3+1, 21+15+14+12+11+9+7+1, 21+15+14+12+11+9+7+3+1, 21+15+14+12+11+9+7+5+1, 21+15+14+12+11+9+7+5+2+1, 21+15+14+12+11+9+7+5+3+1, 21+16+1, 21+16+3+1, 21+16+5+1, 21+16+5+2+1, 21+16+5+3+1, 21+16+7+1, 21+16+7+3+1, 21+16+7+5+1, 21+16+7+5+2+1, 21+16+7+5+3+1, 21+16+9+1, 21+16+9+3+1, 21+16+9+5+1, 21+16+9+5+2+1, 21+16+9+5+3+1, 21+16+9+7+1, 21+16+9+7+3+1, 21+16+9+7+5+1, 21+16+9+7+5+2+1, 21+16+9+7+5+3+1, 21+16+11+1, 21+16+11+3+1, 21+16+11+5+1, 21+16+11+5+2+1, 21+16+11+5+3+1, 21+16+11+7+1, 21+16+11+7+3+1, 21+16+11+7+5+1, 21+16+11+7+5+2+1, 21+16+11+7+5+3+1, 21+16+11+9+1, 21+16+11+9+3+1, 21+16+11+9+5+1, 21+16+11+9+5+2+1, 21+16+11+9+5+3+1, 21+16+11+9+7+1, 21+16+11+9+7+3+1, 21+16+11+9+7+5+1, 21+16+11+9+7+5+2+1, 21+16+11+9+7+5+3+1, 21+16+14+12+1, 21+16+14+12+3+1, 21+16+14+12+5+1, 21+16+14+12+5+2+1, 21+16+14+12+5+3+1, 21+16+14+12+7+1, 21+16+14+12+7+3+1, 21+16+14+12+7+5+1, 21+16+14+12+7+5+2+1, 21+16+14+12+7+5+3+1, 21+16+14+12+9+1, 21+16+14+12+9+3+1, 21+16+14+12+9+5+1, 21+16+14+12+9+5+2+1, 21+16+14+12+9+5+3+1, 21+16+14+12+9+7+1, 21+16+14+12+9+7+3+1, 21+16+14+12+9+7+5+1, 21+16+14+12+9+7+5+2+1, 21+16+14+12+9+7+5+3+1, 21+16+14+12+11+1, 21+16+14+12+11+3+1, 21+16+14+12+11+5+1, 21+16+14+12+11+5+2+1, 21+16+14+12+11+5+3+1, 21+16+14+12+11+7+1, 21+16+14+12+11+7+3+1, 21+16+14+12+11+7+5+1, 21+16+14+12+11+7+5+2+1, 21+16+14+12+11+7+5+3+1, 21+16+14+12+11+9+1, 21+16+14+12+11+9+3+1, 21+16+14+12+11+9+5+1,

21+16+14+12+11+9+5+2+1, 21+16+14+12+11+9+5+3+1, 21+16+14+12+11+9+7+1, 21+16+14+12+11+9+7+3+1, 21+16+14+12+11+9+7+5+1, 21+16+14+12+11+9+7+5+2+1, 21+16+14+12+11+9+7+5+3+1, 21+16+15+1, 21+16+15+3+1, 21+16+15+5+1, 21+16+15+5+2+1, 21+16+15+5+3+1, 21+16+15+7+1, 21+16+15+7+3+1, 21+16+15+7+5+1, 21+16+15+7+5+2+1, 21+16+15+7+5+3+1, 21+16+15+9+1, 21+16+15+9+3+1, 21+16+15+9+5+1, 21+16+15+9+5+2+1, 21+16+15+9+5+3+1, 21+16+15+9+7+1, 21+16+15+9+7+3+1, 21+16+15+9+7+5+1, 21+16+15+9+7+5+2+1, 21+16+15+9+7+5+3+1, 21+16+15+11+1, 21+16+15+11+3+1, 21+16+15+11+5+1, 21+16+15+11+5+2+1, 21+16+15+11+5+3+1, 21+16+15+11+7+1, 21+16+15+11+7+3+1, 21+16+15+11+7+5+1, 21+16+15+11+7+5+2+1, 21+16+15+11+7+5+3+1, 21+16+15+11+9+1, 21+16+15+11+9+3+1, 21+16+15+11+9+5+1, 21+16+15+11+9+5+2+1, 21+16+15+11+9+5+3+1, 21+16+15+11+9+7+1, 21+16+15+11+9+7+3+1, 21+16+15+11+9+7+5+1, 21+16+15+11+9+7+5+2+1, 21+16+15+11+9+7+5+3+1, 21+16+15+14+12+1, 21+16+15+14+12+3+1, 21+16+15+14+12+5+1, 21+16+15+14+12+5+2+1, 21+16+15+14+12+5+3+1, 21+16+15+14+12+7+1, 21+16+15+14+12+7+3+1, 21+16+15+14+12+7+5+1, 21+16+15+14+12+7+5+2+1, 21+16+15+14+12+7+5+3+1, 21+16+15+14+12+9+1, 21+16+15+14+12+9+3+1, 21+16+15+14+12+9+5+1, 21+16+15+14+12+9+5+2+1, 21+16+15+14+12+9+5+3+1, 21+16+15+14+12+9+7+1, 21+16+15+14+12+9+7+3+1, 21+16+15+14+12+9+7+5+1, 21+16+15+14+12+9+7+5+2+1, 21+16+15+14+12+9+7+5+3+1, 21+16+15+14+12+11+1, 21+16+15+14+12+11+3+1, 21+16+15+14+12+11+5+1, 21+16+15+14+12+11+5+2+1, 21+16+15+14+12+11+5+3+1, 21+16+15+14+12+11+7+1, 21+16+15+14+12+11+7+3+1, 21+16+15+14+12+11+7+5+1, 21+16+15+14+12+11+7+5+2+1, 21+16+15+14+12+11+7+5+3+1, 21+16+15+14+12+11+9+1, 21+16+15+14+12+11+9+3+1, 21+16+15+14+12+11+9+5+1, 21+16+15+14+12+11+9+5+2+1, 21+16+15+14+12+11+9+5+3+1, 21+16+15+14+12+11+9+7+1, 21+16+15+14+12+11+9+7+3+1, 21+16+15+14+12+11+9+7+5+1, 21+16+15+14+12+11+9+7+5+2+1, 21+16+15+14+12+11+9+7+5+3+1, 21+19+16+1, 21+19+16+3+1, 21+19+16+5+1, 21+19+16+5+2+1, 21+19+16+5+3+1, 21+19+16+7+1, 21+19+16+7+3+1, 21+19+16+7+5+1, 21+19+16+7+5+2+1, 21+19+16+7+5+3+1, 21+19+16+9+1, 21+19+16+9+3+1, 21+19+16+9+5+1, 21+19+16+9+5+2+1, 21+19+16+9+5+3+1, 21+19+16+9+7+1, 21+19+16+9+7+3+1, 21+19+16+9+7+5+1, 21+19+16+9+7+5+2+1, 21+19+16+9+7+5+3+1, 21+19+16+11+1, 21+19+16+11+3+1, 21+19+16+11+5+1, 21+19+16+11+5+2+1, 21+19+16+11+5+3+1, 21+19+16+11+7+1, 21+19+16+11+7+3+1, 21+19+16+11+7+5+1, 21+19+16+11+7+5+2+1, 21+19+16+11+7+5+3+1, 21+19+16+11+9+1, 21+19+16+11+9+3+1, 21+19+16+11+9+5+1, 21+19+16+11+9+5+2+1, 21+19+16+11+9+5+3+1, 21+19+16+11+9+7+1, 21+19+16+11+9+7+3+1, 21+19+16+11+9+7+5+1, 21+19+16+11+9+7+5+2+1, 21+19+16+11+9+7+5+3+1, 21+19+16+14+12+1, 21+19+16+14+12+3+1, 21+19+16+14+12+5+1, 21+19+16+14+12+5+2+1, 21+19+16+14+12+5+3+1, 21+19+16+14+12+7+1, 21+19+16+14+12+7+3+1, 21+19+16+14+12+7+5+1, 21+19+16+14+12+7+5+2+1, 21+19+16+14+12+7+5+3+1, 21+19+16+14+12+9+1, 21+19+16+14+12+9+3+1, 21+19+16+14+12+9+5+1, 21+19+16+14+12+9+5+2+1, 21+19+16+14+12+9+5+3+1, 21+19+16+14+12+9+7+1, 21+19+16+14+12+9+7+3+1, 21+19+16+14+12+9+7+5+1, 21+19+16+14+12+9+7+5+2+1, 21+19+16+14+12+9+7+5+3+1, 21+19+16+14+12+11+1, 21+19+16+14+12+11+3+1, 21+19+16+14+12+11+5+1, 21+19+16+14+12+11+5+2+1, 21+19+16+14+12+11+5+3+1, 21+19+16+14+12+11+7+1, 21+19+16+14+12+11+7+3+1, 21+19+16+14+12+11+7+5+1, 21+19+16+14+12+11+7+5+2+1, 21+19+16+14+12+11+7+5+3+1, 21+19+16+14+12+11+9+1, 21+19+16+14+12+11+9+3+1, 21+19+16+14+12+11+9+5+1, 21+19+16+14+12+11+9+5+2+1, 21+19+16+14+12+11+9+5+3+1, 21+19+16+14+12+11+9+7+1, 21+19+16+14+12+11+9+7+3+1, 21+19+16+14+12+11+9+7+5+1, 21+19+16+14+12+11+9+7+5+2+1, 21+19+16+14+12+11+9+7+5+3+1, 21+19+16+15+1, 21+19+16+15+3+1, 21+19+16+15+5+1, 21+19+16+15+5+2+1, 21+19+16+15+5+3+1, 21+19+16+15+7+1, 21+19+16+15+7+3+1, 21+19+16+15+7+5+1, 21+19+16+15+7+5+2+1, 21+19+16+15+7+5+3+1, 21+19+16+15+9+1, 21+19+16+15+9+3+1, 21+19+16+15+9+5+1, 21+19+16+15+9+5+2+1, 21+19+16+15+9+5+3+1, 21+19+16+15+9+7+1, 21+19+16+15+9+7+3+1, 21+19+16+15+9+7+5+1, 21+19+16+15+9+7+5+2+1, 21+19+16+15+9+7+5+3+1, 21+19+16+15+11+1, 21+19+16+15+11+3+1, 21+19+16+15+11+5+1, 21+19+16+15+11+5+2+1, 21+19+16+15+11+5+3+1, 21+19+16+15+11+7+1, 21+19+16+15+11+7+3+1, 21+19+16+15+11+7+5+1, 21+19+16+15+11+7+5+2+1, 21+19+16+15+11+7+5+3+1, 21+19+16+15+11+9+1, 21+19+16+15+11+9+3+1, 21+19+16+15+11+9+5+1, 21+19+16+15+11+9+5+2+1, 21+19+16+15+11+9+5+3+1, 21+19+16+15+11+9+7+1, 21+19+16+15+11+9+7+3+1, 21+19+16+15+11+9+7+5+1, 21+19+16+15+11+9+7+5+2+1, 21+19+16+15+11+9+7+5+3+1, 21+19+16+15+14+12+1, 21+19+16+15+14+12+3+1, 21+19+16+15+14+12+5+1, 21+19+16+15+14+12+5+2+1, 21+19+16+15+14+12+5+3+1, 21+19+16+15+14+12+7+1, 21+19+16+15+14+12+7+3+1, 21+19+16+15+14+12+7+5+1, 21+19+16+15+14+12+7+5+2+1, 21+19+16+15+14+12+7+5+3+1, 21+19+16+15+14+12+9+1, 21+19+16+15+14+12+9+3+1, 21+19+16+15+14+12+9+5+1, 21+19+16+15+14+12+9+5+2+1, 21+19+16+15+14+12+9+5+3+1, 21+19+16+15+14+12+9+7+1, 21+19+16+15+14+12+9+7+3+1, 21+19+16+15+14+12+9+7+5+1, 21+19+16+15+14+12+9+7+5+2+1, 21+19+16+15+14+12+9+7+5+3+1, 21+19+16+15+14+12+11+1, 21+19+16+15+14+12+11+3+1, 21+19+16+15+14+12+11+5+1, 21+19+16+15+14+12+11+5+2+1, 21+19+16+15+14+12+11+5+3+1, 21+19+16+15+14+12+11+7+1, 21+19+16+15+14+12+11+7+3+1, 21+19+16+15+14+12+11+7+5+1, 21+19+16+15+14+12+11+7+5+2+1, 21+19+16+15+14+12+11+7+5+3+1, 21+19+16+15+14+12+11+9+1, 21+19+16+15+14+12+11+9+3+1, 21+19+16+15+14+12+11+9+5+1, 21+19+16+15+14+12+11+9+5+2+1, 21+19+16+15+14+12+11+9+5+3+1, 21+19+16+15+14+12+11+9+7+1, 21+19+16+15+14+12+11+9+7+3+1, 21+19+16+15+14+12+11+9+7+5+1, 21+19+16+15+14+12+11+9+7+5+2+1, 21+19+16+15+14+12+11+9+7+5+3+1, 22+21+1, 22+21+3+1, 22+21+5+1, 22+21+5+2+1, 22+21+5+3+1, 22+21+7+1, 22+21+7+3+1, 22+21+7+5+1, 22+21+7+5+2+1, 22+21+7+5+3+1, 22+21+9+1, 22+21+9+3+1, 22+21+9+5+1, 22+21+9+5+2+1, 22+21+9+5+3+1, 22+21+9+7+1, 22+21+9+7+3+1, 22+21+9+7+5+1, 22+21+9+7+5+2+1, 22+21+9+7+5+3+1, 22+21+11+1, 22+21+11+3+1, 22+21+11+5+1, 22+21+11+5+2+1, 22+21+11+5+3+1, 22+21+11+7+1, 22+21+11+7+3+1, 22+21+11+7+5+1, 22+21+11+7+5+2+1, 22+21+11+7+5+3+1, 22+21+11+9+1, 22+21+11+9+3+1, 22+21+11+9+5+1, 22+21+11+9+5+2+1, 22+21+11+9+5+3+1, 22+21+11+9+7+1, 22+21+11+9+7+3+1, 22+21+11+9+7+5+1, 22+21+11+9+7+5+2+1, 22+21+11+9+7+5+3+1, 22+21+14+12+1, 22+21+14+12+3+1, 22+21+14+12+5+1, 22+21+14+12+5+2+1, 22+21+14+12+5+3+1, 22+21+14+12+7+1, 22+21+14+12+7+3+1, 22+21+14+12+7+5+1, 22+21+14+12+7+5+2+1, 22+21+14+12+7+5+3+1, 22+21+14+12+9+1, 22+21+14+12+9+3+1, 22+21+14+12+9+5+1, 22+21+14+12+9+5+2+1, 22+21+14+12+9+5+3+1, 22+21+14+12+9+7+1, 22+21+14+12+9+7+3+1, 22+21+14+12+9+

7+5+1, 22+21+14+12+9+7+5+2+1, 22+21+14+12+9+7+5+3+1, 22+21+14+12+11+1, 22+21+14+12+11+3+1, 22+21+14+12+11+5+1, 22+21+14+12+11+5+2+1, 22+21+14+12+11+5+3+1, 22+21+14+12+11+7+1, 22+21+14+12+11+7+3+1, 22+21+14+12+11+7+5+1, 22+21+14+12+11+7+5+2+1, 22+21+14+12+11+7+5+3+1, 22+21+14+12+11+9+1, 22+21+14+12+11+9+3+1, 22+21+14+12+11+9+5+1, 22+21+14+12+11+9+5+2+1, 22+21+14+12+11+9+5+3+1, 22+21+14+12+11+9+7+1, 22+21+14+12+11+9+7+3+1, 22+21+14+12+11+9+7+5+1, 22+21+14+12+11+9+7+5+2+1, 22+21+14+12+11+9+7+5+3+1, 22+21+15+1, 22+21+15+3+1, 22+21+15+5+1, 22+21+15+5+2+1, 22+21+15+5+3+1, 22+21+15+7+1, 22+21+15+7+3+1, 22+21+15+7+5+1, 22+21+15+7+5+2+1, 22+21+15+7+5+3+1, 22+21+15+9+1, 22+21+15+9+3+1, 22+21+15+9+5+1, 22+21+15+9+5+2+1, 22+21+15+9+5+3+1, 22+21+15+9+7+1, 22+21+15+9+7+3+1, 22+21+15+9+7+5+1, 22+21+15+9+7+5+2+1, 22+21+15+9+7+5+3+1, 22+21+15+11+1, 22+21+15+11+3+1, 22+21+15+11+5+1, 22+21+15+11+5+2+1, 22+21+15+11+5+3+1, 22+21+15+11+7+1, 22+21+15+11+7+3+1, 22+21+15+11+7+5+1, 22+21+15+11+7+5+2+1, 22+21+15+11+7+5+3+1, 22+21+15+11+9+1, 22+21+15+11+9+3+1, 22+21+15+11+9+5+1, 22+21+15+11+9+5+2+1, 22+21+15+11+9+5+3+1, 22+21+15+11+9+7+1, 22+21+15+11+9+7+3+1, 22+21+15+11+9+7+5+1, 22+21+15+11+9+7+5+2+1, 22+21+15+11+9+7+5+3+1, 22+21+15+14+12+1, 22+21+15+14+12+3+1, 22+21+15+14+12+5+1, 22+21+15+14+12+5+2+1, 22+21+15+14+12+5+3+1, 22+21+15+14+12+7+1, 22+21+15+14+12+7+3+1, 22+21+15+14+12+7+5+1, 22+21+15+14+12+7+5+2+1, 22+21+15+14+12+7+5+3+1, 22+21+15+14+12+9+1, 22+21+15+14+12+9+3+1, 22+21+15+14+12+9+5+1, 22+21+15+14+12+9+5+2+1, 22+21+15+14+12+9+5+3+1, 22+21+15+14+12+9+7+1, 22+21+15+14+12+9+7+3+1, 22+21+15+14+12+9+7+5+1, 22+21+15+14+12+9+7+5+2+1, 22+21+15+14+12+9+7+5+3+1, 22+21+15+14+12+11+1, 22+21+15+14+12+11+3+1, 22+21+15+14+12+11+5+1, 22+21+15+14+12+11+5+2+1, 22+21+15+14+12+11+5+3+1, 22+21+15+14+12+11+7+1, 22+21+15+14+12+11+7+3+1, 22+21+15+14+12+11+7+5+1, 22+21+15+14+12+11+7+5+2+1, 22+21+15+14+12+11+7+5+3+1, 22+21+15+14+12+11+9+1, 22+21+15+14+12+11+9+3+1, 22+21+15+14+12+11+9+5+1, 22+21+15+14+12+11+9+5+2+1, 22+21+15+14+12+11+9+5+3+1, 22+21+15+14+12+11+9+7+1, 22+21+15+14+12+11+9+7+3+1, 22+21+15+14+12+11+9+7+5+1, 22+21+15+14+12+11+9+7+5+2+1, 22+21+15+14+12+11+9+7+5+3+1, 22+21+16+1, 22+21+16+3+1, 22+21+16+5+1, 22+21+16+5+2+1, 22+21+16+5+3+1, 22+21+16+7+1, 22+21+16+7+3+1, 22+21+16+7+5+1, 22+21+16+7+5+2+1, 22+21+16+7+5+3+1, 22+21+16+9+1, 22+21+16+9+3+1, 22+21+16+9+5+1, 22+21+16+9+5+2+1, 22+21+16+9+5+3+1, 22+21+16+9+7+1, 22+21+16+9+7+3+1, 22+21+16+9+7+5+1, 22+21+16+9+7+5+2+1, 22+21+16+9+7+5+3+1, 22+21+16+11+1, 22+21+16+11+3+1, 22+21+16+11+5+1, 22+21+16+11+5+2+1, 22+21+16+11+5+3+1, 22+21+16+11+7+1, 22+21+16+11+7+3+1, 22+21+16+11+7+5+1, 22+21+16+11+7+5+2+1, 22+21+16+11+7+5+3+1, 22+21+16+11+9+1, 22+21+16+11+9+3+1, 22+21+16+11+9+5+1, 22+21+16+11+9+5+2+1, 22+21+16+11+9+5+3+1, 22+21+16+11+9+7+1, 22+21+16+11+9+7+3+1, 22+21+16+11+9+7+5+1, 22+21+16+11+9+7+5+2+1, 22+21+16+11+9+7+5+3+1, 22+21+16+14+12+1, 22+21+16+14+12+3+1, 22+21+16+14+12+5+1, 22+21+16+14+12+5+2+1, 22+21+16+14+12+5+3+1, 22+21+16+14+12+7+1, 22+21+16+14+12+7+3+1, 22+21+16+14+12+7+5+1, 22+21+16+14+12+7+5+2+1, 22+21+16+14+12+7+5+3+1, 22+21+16+14+12+9+1, 22+21+16+14+12+9+3+1, 22+21+16+14+12+9+5+1, 22+21+16+14+12+9+5+2+1, 22+21+16+14+12+9+5+3+1, 22+21+16+14+12+9+7+1, 22+21+16+14+12+9+7+3+1, 22+21+16+14+12+9+7+5+1, 22+21+16+14+12+9+7+5+2+1, 22+21+16+14+12+9+7+5+3+1, 22+21+16+14+12+11+1, 22+21+16+14+12+11+3+1, 22+21+16+14+12+11+5+1, 22+21+16+14+12+11+5+2+1, 22+21+16+14+12+11+5+3+1, 22+21+16+14+12+11+7+1, 22+21+16+14+12+11+7+3+1, 22+21+16+14+12+11+7+5+1, 22+21+16+14+12+11+7+5+2+1, 22+21+16+14+12+11+7+5+3+1, 22+21+16+14+12+11+9+1, 22+21+16+14+12+11+9+3+1, 22+21+16+14+12+11+9+5+1, 22+21+16+14+12+11+9+5+2+1, 22+21+16+14+12+11+9+5+3+1, 22+21+16+14+12+11+9+7+1, 22+21+16+14+12+11+9+7+3+1, 22+21+16+14+12+11+9+7+5+1, 22+21+16+14+12+11+9+7+5+2+1, 22+21+16+14+12+11+9+7+5+3+1, 22+21+16+15+1, 22+21+16+15+3+1, 22+21+16+15+5+1, 22+21+16+15+5+2+1, 22+21+16+15+5+3+1, 22+21+16+15+7+1, 22+21+16+15+7+3+1, 22+21+16+15+7+5+1, 22+21+16+15+7+5+2+1, 22+21+16+15+7+5+3+1, 22+21+16+15+9+1, 22+21+16+15+9+3+1, 22+21+16+15+9+5+1, 22+21+16+15+9+5+2+1, 22+21+16+15+9+5+3+1, 22+21+16+15+9+7+1, 22+21+16+15+9+7+3+1, 22+21+16+15+9+7+5+1, 22+21+16+15+9+7+5+2+1, 22+21+16+15+9+7+5+3+1, 22+21+16+15+11+1, 22+21+16+15+11+3+1, 22+21+16+15+11+5+1, 22+21+16+15+11+5+2+1, 22+21+16+15+11+5+3+1, 22+21+16+15+11+7+1, 22+21+16+15+11+7+3+1, 22+21+16+15+11+7+5+1, 22+21+16+15+11+7+5+2+1, 22+21+16+15+11+7+5+3+1, 22+21+16+15+11+9+1, 22+21+16+15+11+9+3+1, 22+21+16+15+11+9+5+1, 22+21+16+15+11+9+5+2+1, 22+21+16+15+11+9+5+3+1, 22+21+16+15+11+9+7+1, 22+21+16+15+11+9+7+3+1, 22+21+16+15+11+9+7+5+1, 22+21+16+15+11+9+7+5+2+1, 22+21+16+15+11+9+7+5+3+1, 22+21+16+15+14+12+1, 22+21+16+15+14+12+3+1, 22+21+16+15+14+12+5+1, 22+21+16+15+14+12+5+2+1, 22+21+16+15+14+12+5+3+1, 22+21+16+15+14+12+7+1, 22+21+16+15+14+12+7+3+1, 22+21+16+15+14+12+7+5+1, 22+21+16+15+14+12+7+5+2+1, 22+21+16+15+14+12+7+5+3+1, 22+21+16+15+14+12+9+1, 22+21+16+15+14+12+9+3+1, 22+21+16+15+14+12+9+5+1, 22+21+16+15+14+12+9+5+2+1, 22+21+16+15+14+12+9+5+3+1, 22+21+16+15+14+12+9+7+1, 22+21+16+15+14+12+9+7+3+1, 22+21+16+15+14+12+9+7+5+1, 22+21+16+15+14+12+9+7+5+2+1, 22+21+16+15+14+12+9+7+5+3+1, 22+21+16+15+14+12+11+1, 22+21+16+15+14+12+11+3+1, 22+21+16+15+14+12+11+5+1, 22+21+16+15+14+12+11+5+2+1, 22+21+16+15+14+12+11+5+3+1, 22+21+16+15+14+12+11+7+1, 22+21+16+15+14+12+11+7+3+1, 22+21+16+15+14+12+11+7+5+1, 22+21+16+15+14+12+11+7+5+2+1, 22+21+16+15+14+12+11+7+5+3+1, 22+21+16+15+14+12+11+9+1, 22+21+16+15+14+12+11+9+3+1, 22+21+16+15+14+12+11+9+5+1, 22+21+16+15+14+12+11+9+5+2+1, 22+21+16+15+14+12+11+9+5+3+1, 22+21+16+15+14+12+11+9+7+1, 22+21+16+15+14+12+11+9+7+3+1, 22+21+16+15+14+12+11+9+7+5+1, 22+21+16+15+14+12+11+9+7+5+2+1, 22+21+16+15+14+12+11+9+7+5+3+1, 22+21+19+16+1, 22+21+19+16+3+1, 22+21+19+16+5+1, 22+21+19+16+5+2+1, 22+21+19+16+5+3+1, 22+21+19+16+7+1, 22+21+19+16+7+3+1, 22+21+19+16+7+5+1, 22+21+19+16+7+5+2+1, 22+21+19+16+7+5+3+1, 22+21+19+16+9+1, 22+21+19+16+9+3+1, 22+21+19+16+9+5+1, 22+21+19+16+9+5+2+1, 22+21+19+16+9+5+3+1, 22+21+19+16+9+7+1, 22+21+19+16+9+7+3+1, 22+21+19+16+9+7+5+1, 22+21+19+16+9+7+5+2+1, 22+21+19+16+9+7+5+3+1, 22+21+19+16+11+1, 22+21+19+16+11+3+1, 22+21+19+16+11+5+1, 22+21+19+16+11+5+2+1, 22+21+19+16+11+5+3+1, 22+21+19+16+11+7+1, 22+21+19+16+11+7+3+1, 22+21+19+16+11+7+5+1, 22+21+19+16+11+7+5+2+1, 22+21+

19+16+11+7+5+3+1, 22+21+19+16+11+9+1, 22+21+19+16+11+9+3+1, 22+21+19+16+11+9+5+1, 22+21+19+16+11+9+5+2+1, 22+21+19+16+11+9+5+3+1, 22+21+19+16+11+9+7+1, 22+21+19+16+11+9+7+3+1, 22+21+19+16+11+9+7+5+1, 22+21+19+16+11+9+7+5+2+1, 22+21+19+16+11+9+7+5+3+1, 22+21+19+16+14+12+1, 22+21+19+16+14+12+3+1, 22+21+19+16+14+12+5+1, 22+21+19+16+14+12+5+2+1, 22+21+19+16+14+12+5+3+1, 22+21+19+16+14+12+7+1, 22+21+19+16+14+12+7+3+1, 22+21+19+16+14+12+7+5+1, 22+21+19+16+14+12+7+5+2+1, 22+21+19+16+14+12+7+5+3+1, 22+21+19+16+14+12+9+1, 22+21+19+16+14+12+9+3+1, 22+21+19+16+14+12+9+5+1, 22+21+19+16+14+12+9+5+2+1, 22+21+19+16+14+12+9+5+3+1, 22+21+19+16+14+12+9+7+1, 22+21+19+16+14+12+9+7+3+1, 22+21+19+16+14+12+9+7+5+1, 22+21+19+16+14+12+9+7+5+2+1, 22+21+19+16+14+12+9+7+5+3+1, 22+21+19+16+14+12+11+1, 22+21+19+16+14+12+11+3+1, 22+21+19+16+14+12+11+5+1, 22+21+19+16+14+12+11+5+2+1, 22+21+19+16+14+12+11+5+3+1, 22+21+19+16+14+12+11+7+1, 22+21+19+16+14+12+11+7+3+1, 22+21+19+16+14+12+11+7+5+1, 22+21+19+16+14+12+11+7+5+2+1, 22+21+19+16+14+12+11+7+5+3+1, 22+21+19+16+14+12+11+9+1, 22+21+19+16+14+12+11+9+3+1, 22+21+19+16+14+12+11+9+5+1, 22+21+19+16+14+12+11+9+5+2+1, 22+21+19+16+14+12+11+9+5+3+1, 22+21+19+16+14+12+11+9+7+1, 22+21+19+16+14+12+11+9+7+3+1, 22+21+19+16+14+12+11+9+7+5+1, 22+21+19+16+14+12+11+9+7+5+2+1, 22+21+19+16+14+12+11+9+7+5+3+1, 22+21+19+16+15+1, 22+21+19+16+15+3+1, 22+21+19+16+15+5+1, 22+21+19+16+15+5+2+1, 22+21+19+16+15+5+3+1, 22+21+19+16+15+7+1, 22+21+19+16+15+7+3+1, 22+21+19+16+15+7+5+1, 22+21+19+16+15+7+5+2+1, 22+21+19+16+15+7+5+3+1, 22+21+19+16+15+9+1, 22+21+19+16+15+9+3+1, 22+21+19+16+15+9+5+1, 22+21+19+16+15+9+5+2+1, 22+21+19+16+15+9+5+3+1, 22+21+19+16+15+9+7+1, 22+21+19+16+15+9+7+3+1, 22+21+19+16+15+9+7+5+1, 22+21+19+16+15+9+7+5+2+1, 22+21+19+16+15+9+7+5+3+1, 22+21+19+16+15+11+1, 22+21+19+16+15+11+3+1, 22+21+19+16+15+11+5+1, 22+21+19+16+15+11+5+2+1, 22+21+19+16+15+11+5+3+1, 22+21+19+16+15+11+7+1, 22+21+19+16+15+11+7+3+1, 22+21+19+16+15+11+7+5+1, 22+21+19+16+15+11+7+5+2+1, 22+21+19+16+15+11+7+5+3+1, 22+21+19+16+15+11+9+1, 22+21+19+16+15+11+9+3+1, 22+21+19+16+15+11+9+5+1, 22+21+19+16+15+11+9+5+2+1, 22+21+19+16+15+11+9+5+3+1, 22+21+19+16+15+11+9+7+1, 22+21+19+16+15+11+9+7+3+1, 22+21+19+16+15+11+9+7+5+1, 22+21+19+16+15+11+9+7+5+2+1, 22+21+19+16+15+11+9+7+5+3+1, 22+21+19+16+15+14+12+1, 22+21+19+16+15+14+12+3+1, 22+21+19+16+15+14+12+5+1, 22+21+19+16+15+14+12+5+2+1, 22+21+19+16+15+14+12+5+3+1, 22+21+19+16+15+14+12+7+1, 22+21+19+16+15+14+12+7+3+1, 22+21+19+16+15+14+12+7+5+1, 22+21+19+16+15+14+12+7+5+2+1, 22+21+19+16+15+14+12+7+5+3+1, 22+21+19+16+15+14+12+9+1, 22+21+19+16+15+14+12+9+3+1, 22+21+19+16+15+14+12+9+5+1, 22+21+19+16+15+14+12+9+5+2+1, 22+21+19+16+15+14+12+9+5+3+1, 22+21+19+16+15+14+12+9+7+1, 22+21+19+16+15+14+12+9+7+3+1, 22+21+19+16+15+14+12+9+7+5+1, 22+21+19+16+15+14+12+9+7+5+2+1, 22+21+19+16+15+14+12+9+7+5+3+1, 22+21+19+16+15+14+12+11+1, 22+21+19+16+15+14+12+11+3+1, 22+21+19+16+15+14+12+11+5+1, 22+21+19+16+15+14+12+11+5+2+1, 22+21+19+16+15+14+12+11+5+3+1, 22+21+19+16+15+14+12+11+7+1, 22+21+19+16+15+14+12+11+7+3+1, 22+21+19+16+15+14+12+11+7+5+1, 22+21+19+16+15+14+12+11+7+5+2+1, 22+21+19+16+15+14+12+11+7+5+3+1, 22+21+19+16+15+14+12+11+9+1, 22+21+19+16+15+14+12+11+9+3+1, 22+21+19+16+15+14+12+11+9+5+1, 22+21+19+16+15+14+12+11+9+5+2+1, 22+21+19+16+15+14+12+11+9+5+3+1, 22+21+19+16+15+14+12+11+9+7+1, 22+21+19+16+15+14+12+11+9+7+3+1, 22+21+19+16+15+14+12+11+9+7+5+1, 22+21+19+16+15+14+12+11+9+7+5+2+1, 22+21+19+16+15+14+12+11+9+7+5+3+1, 23+1, 23+3+1, 23+5+1, 23+5+2+1, 23+5+3+1, 23+7+1, 23+7+3+1, 23+7+5+1, 23+7+5+2+1, 23+7+5+3+1, 23+9+1, 23+9+3+1, 23+9+5+1, 23+9+5+2+1, 23+9+5+3+1, 23+9+7+1, 23+9+7+3+1, 23+9+7+5+1, 23+9+7+5+2+1, 23+9+7+5+3+1, 23+11+1, 23+11+3+1, 23+11+5+1, 23+11+5+2+1, 23+11+5+3+1, 23+11+7+1, 23+11+7+3+1, 23+11+7+5+1, 23+11+7+5+2+1, 23+11+7+5+3+1, 23+11+9+1, 23+11+9+3+1, 23+11+9+5+1, 23+11+9+5+2+1, 23+11+9+5+3+1, 23+11+9+7+1, 23+11+9+7+3+1, 23+11+9+7+5+1, 23+11+9+7+5+2+1, 23+11+9+7+5+3+1, 23+14+12+1, 23+14+12+3+1, 23+14+12+5+1, 23+14+12+5+2+1, 23+14+12+5+3+1, 23+14+12+7+1, 23+14+12+7+3+1, 23+14+12+7+5+1, 23+14+12+7+5+2+1, 23+14+12+7+5+3+1, 23+14+12+9+1, 23+14+12+9+3+1, 23+14+12+9+5+1, 23+14+12+9+5+2+1, 23+14+12+9+5+3+1, 23+14+12+9+7+1, 23+14+12+9+7+3+1, 23+14+12+9+7+5+1, 23+14+12+9+7+5+2+1, 23+14+12+9+7+5+3+1, 23+14+12+11+1, 23+14+12+11+3+1, 23+14+12+11+5+1, 23+14+12+11+5+2+1, 23+14+12+11+5+3+1, 23+14+12+11+7+1, 23+14+12+11+7+3+1, 23+14+12+11+7+5+1, 23+14+12+11+7+5+2+1, 23+14+12+11+7+5+3+1, 23+14+12+11+9+1, 23+14+12+11+9+3+1, 23+14+12+11+9+5+1, 23+14+12+11+9+5+2+1, 23+14+12+11+9+5+3+1, 23+14+12+11+9+7+1, 23+14+12+11+9+7+3+1, 23+14+12+11+9+7+5+1, 23+14+12+11+9+7+5+2+1, 23+14+12+11+9+7+5+3+1, 23+15+1, 23+15+3+1, 23+15+5+1, 23+15+5+2+1, 23+15+5+3+1, 23+15+7+1, 23+15+7+3+1, 23+15+7+5+1, 23+15+7+5+2+1, 23+15+7+5+3+1, 23+15+9+1, 23+15+9+3+1, 23+15+9+5+1, 23+15+9+5+2+1, 23+15+9+5+3+1, 23+15+9+7+1, 23+15+9+7+3+1, 23+15+9+7+5+1, 23+15+9+7+5+2+1, 23+15+9+7+5+3+1, 23+15+11+1, 23+15+11+3+1, 23+15+11+5+1, 23+15+11+5+2+1, 23+15+11+5+3+1, 23+15+11+7+1, 23+15+11+7+3+1, 23+15+11+7+5+1, 23+15+11+7+5+2+1, 23+15+11+7+5+3+1, 23+15+11+9+1, 23+15+11+9+3+1, 23+15+11+9+5+1, 23+15+11+9+5+2+1, 23+15+11+9+5+3+1, 23+15+11+9+7+1, 23+15+11+9+7+3+1, 23+15+11+9+7+5+1, 23+15+11+9+7+5+2+1, 23+15+11+9+7+5+3+1, 23+15+14+12+1, 23+15+14+12+3+1, 23+15+14+12+5+1, 23+15+14+12+5+2+1, 23+15+14+12+5+3+1, 23+15+14+12+7+1, 23+15+14+12+7+3+1, 23+15+14+12+7+5+1, 23+15+14+12+7+5+2+1, 23+15+14+12+7+5+3+1, 23+15+14+12+9+1, 23+15+14+12+9+3+1, 23+15+14+12+9+5+1, 23+15+14+12+9+5+2+1, 23+15+14+12+9+5+3+1, 23+15+14+12+9+7+1, 23+15+14+12+9+7+3+1, 23+15+14+12+9+7+5+1, 23+15+14+12+9+7+5+2+1, 23+15+14+12+9+7+5+3+1, 23+15+14+12+11+1, 23+15+14+12+11+3+1, 23+15+14+12+11+5+1, 23+15+14+12+11+5+2+1, 23+15+14+12+11+5+3+1, 23+15+14+12+11+7+1, 23+15+14+12+11+7+3+1, 23+15+14+12+11+7+5+1, 23+15+14+12+11+7+5+2+1, 23+15+14+12+11+7+5+3+1, 23+15+14+12+11+9+1, 23+15+14+12+11+9+3+1, 23+15+14+12+11+9+5+1, 23+15+14+12+11+9+5+2+1, 23+15+14+12+11+9+5+3+1, 23+15+14+12+11+9+7+1, 23+15+14+12+11+9+7+3+1, 23+15+14+12+11+9+7+5+1, 23+15+14+12+11+9+7+5+2+1, 23+15+14+12+11+9+7+5+3+1, 24, 25+24, 26+24, 27+24, 27+25+24, 27+26+24, 28+27+24, 28+27+25+24, 28+27+26+24, 29+27+24, 29+27+25+24, 29+27+26+24, 30+27+24, 30+27+25+24, 30+27+26+24, 30+28+27+24, 30+28+27+25+24, 30+28+27+26+24, 30+29+27+24, 30+29+27+25+24, 30+29+27+26+24, 31+27+24, 31+27+

25+24, 31+27+26+24, 31+28+27+24, 31+28+27+25+24, 31+28+27+26+24, 31+29+27+24, 31+29+27+25+24, 31+29+27+26+24, 32+31+27+24, 32+31+27+25+24, 32+31+27+26+24, 32+31+28+27+24, 32+31+28+27+25+24, 32+31+28+27+26+24, 32+31+29+27+24, 32+31+29+27+25+24, 32+31+29+27+26+24, 33+27+24, 33+27+25+24, 33+27+26+24, 33+28+27+24, 33+28+27+25+24, 33+28+27+26+24, 33+29+27+24, 33+29+27+25+24, 33+29+27+26+24, 34, 35+34, 36+35+34, 37+36+35+34, 38+36+35+34, 39+35+34, 40+34, 40+35+34, 40+36+35+34, 40+37+36+35+34, 40+38+36+35+34, 40+39+35+34, 41+40+34, 41+40+35+34, 41+40+36+35+34, 41+40+37+36+35+34, 41+40+38+36+35+34, 41+40+39+35+34, 42+41+40+34, 42+41+40+35+34, 42+41+40+36+35+34, 42+41+40+37+36+35+34, 42+41+40+38+36+35+34, 42+41+40+39+35+34, 43+41+40+34, 43+41+40+35+34, 43+41+40+36+35+34, 43+41+40+37+36+35+34, 43+41+40+38+36+35+34, 43+41+40+39+35+34, 44+41+40+34, 44+41+40+35+34, 44+41+40+36+35+34, 44+41+40+37+36+35+34, 44+41+40+38+36+35+34, 44+41+40+39+35+34, 44+42+41+40+34, 44+42+41+40+35+34, 44+42+41+40+36+35+34, 44+42+41+40+37+36+35+34, 44+42+41+40+38+36+35+34, 44+42+41+40+39+35+34, 44+43+41+40+34, 44+43+41+40+35+34, 44+43+41+40+36+35+34, 44+43+41+40+37+36+35+34, 44+43+41+40+38+36+35+34, 44+43+41+40+39+35+34, 45+44+41+40+34, 45+44+41+40+35+34, 45+44+41+40+36+35+34, 45+44+41+40+37+36+35+34, 45+44+41+40+38+36+35+34, 45+44+41+40+39+35+34, 45+44+42+41+40+34, 45+44+42+41+40+35+34, 45+44+42+41+40+36+35+34, 45+44+42+41+40+37+36+35+34, 45+44+42+41+40+38+36+35+34, 45+44+42+41+40+39+35+34, 45+44+43+41+40+34, 45+44+43+41+40+35+34, 45+44+43+41+40+36+35+34, 45+44+43+41+40+37+36+35+34, 45+44+43+41+40+38+36+35+34, 45+44+43+41+40+39+35+34, 46+44+41+40+34, 46+44+41+40+35+34, 46+44+41+40+36+35+34, 46+44+41+40+37+36+35+34, 46+44+41+40+38+36+35+34, 46+44+41+40+39+35+34, 46+44+42+41+40+34, 46+44+42+41+40+35+34, 46+44+42+41+40+36+35+34, 46+44+42+41+40+37+36+35+34, 46+44+42+41+40+38+36+35+34, 46+44+42+41+40+39+35+34, 46+44+43+41+40+34, 46+44+43+41+40+35+34, 46+44+43+41+40+36+35+34, 46+44+43+41+40+37+36+35+34, 46+44+43+41+40+38+36+35+34, 46+44+43+41+40+39+35+34, 47+34, 48+47+34, 49+47+34, 50+47+34, 50+48+47+34, 50+49+47+34, 51+50+47+34, 51+50+48+47+34, 51+50+49+47+34, 52+50+47+34, 52+50+48+47+34, 52+50+49+47+34, 53, 54+53, 55+53, 55+54+53, 56+53, 56+54+53, 57+53, 57+54+53, 57+55+53, 57+55+54+53, 57+56+53, 57+56+54+53, 58+53, 58+54+53, 58+55+53, 58+55+54+53, 58+56+53, 58+56+54+53, 59+53, 59+54+53, 60+53, 60+54+53, 60+55+53, 60+55+54+53, 60+56+53, 60+56+54+53, 60+57+53, 60+57+54+53, 60+57+55+53, 60+57+55+54+53, 60+57+56+53, 60+57+56+54+53, 60+58+53, 60+58+54+53, 60+58+55+53, 60+58+55+54+53, 60+58+56+53, 60+58+56+54+53, 60+59+53, 60+59+54+53, 61+60+53, 61+60+54+53, 61+60+55+53, 61+60+55+54+53, 61+60+56+53, 61+60+56+54+53, 61+60+57+53, 61+60+57+54+53, 61+60+57+55+53, 61+60+57+55+54+53, 61+60+57+56+53, 61+60+57+56+54+53, 61+60+58+53, 61+60+58+54+53, 61+60+58+55+53, 61+60+58+55+54+53, 61+60+58+56+53, 61+60+58+56+54+53, 61+60+59+53, 61+60+59+54+53, 62+60+53, 62+60+54+53, 62+60+55+53, 62+60+55+54+53, 62+60+56+53, 62+60+56+54+53, 62+60+57+53, 62+60+57+54+53, 62+60+57+55+53, 62+60+57+55+54+53, 62+60+57+56+53, 62+60+57+56+54+53, 62+60+58+53, 62+60+58+54+53, 62+60+58+55+53, 62+60+58+55+54+53, 62+60+58+56+53, 62+60+58+56+54+53, 62+60+59+53, 62+60+59+54+53, 63+53, 64+63+53, 65+63+53, 65+64+63+53, 66+53, 66+54+53, 66+56+53, 66+56+54+53, 66+58+53, 66+58+54+53, 66+58+55+53, 66+58+55+54+53, 66+58+56+53, 66+58+56+54+53, 66+59+53, 66+59+54+53, 66+60+53, 66+60+54+53, 66+60+55+53, 66+60+55+54+53, 66+60+56+53, 66+60+56+54+53, 66+60+57+53, 66+60+57+54+53, 66+60+57+55+53, 66+60+57+55+54+53, 66+60+57+56+53, 66+60+57+56+54+53, 66+60+58+53, 66+60+58+54+53, 66+60+58+55+53, 66+60+58+55+54+53, 66+60+58+56+53, 66+60+58+56+54+53, 66+60+59+53, 66+60+59+54+53, 66+62+60+53, 66+62+60+54+53, 66+62+60+55+53, 66+62+60+55+54+53, 66+62+60+56+53, 66+62+60+56+54+53, 66+62+60+57+53, 66+62+60+57+54+53, 66+62+60+57+55+53, 66+62+60+57+55+54+53, 66+62+60+57+56+53, 66+62+60+57+56+54+53, 66+62+60+58+53, 66+62+60+58+54+53, 66+62+60+58+55+53, 66+62+60+58+55+54+53, 66+62+60+58+56+53, 66+62+60+58+56+54+53, 66+62+60+59+53, 66+62+60+59+54+53, 66+63+53, 66+65+63+53, 66+65+64+63+53, 67+53, 67+54+53, 67+56+53, 67+56+54+53, 67+58+53, 67+58+54+53, 67+58+55+53, 67+58+55+54+53, 67+58+56+53, 67+58+56+54+53, 67+59+53, 67+59+54+53, 67+60+53, 67+60+54+53, 67+60+55+53, 67+60+55+54+53, 67+60+56+53, 67+60+56+54+53, 67+60+57+53, 67+60+57+54+53, 67+60+57+55+53, 67+60+57+55+54+53, 67+60+57+56+53, 67+60+57+56+54+53, 67+60+58+53, 67+60+58+54+53, 67+60+58+55+53, 67+60+58+55+54+53, 67+60+58+56+53, 67+60+58+56+54+53, 67+60+59+53, 67+60+59+54+53, 67+62+60+53, 67+62+60+54+53, 67+62+60+55+53, 67+62+60+55+54+53, 67+62+60+56+53, 67+62+60+56+54+53, 67+62+60+57+53, 67+62+60+57+54+53, 67+62+60+57+55+53, 67+62+60+57+55+54+53, 67+62+60+57+56+53, 67+62+60+57+56+54+53, 67+62+60+58+53, 67+62+60+58+54+53, 67+62+60+58+55+53, 67+62+60+58+55+54+53, 67+62+60+58+56+53, 67+62+60+58+56+54+53, 67+62+60+59+53, 67+62+60+59+54+53, 67+63+53, 67+65+63+53 and 67+65+64+63+53.

In the list above, the numbers refer to the embodiments according to their numbering provided hereinabove whereas "+" indicates the dependency from another embodiment.

The different individualised embodiments are separated by commas. In other words, "5+2+1" for example refers to embodiment 5) depending on embodiment 2), depending on embodiment 1), i.e. embodiment "5+2+1" corresponds to embodiment 1) further limited by the features of embodiments 2) and 5). Likewise, "9+7+3+1" refers to embodiment 9) depending mutatis mutandis on embodiments 7) and 3), depending on embodiment 1), i.e. embodiment "9+7+3+1" corresponds to embodiment 1) further limited by the features of embodiment 3), further limited by the features of embodiments 7) and 9).

Methods for preparing the starting compound, i.e. the compounds of formulae I-1 and 1-2 as defined in embodiment 1), are described in the section "Preparation of starting materials" hereafter, while methods for obtaining the compound of formula I from the compound of formula I-1 and the compound of formula I-2 as defined in embodiment 1) are described in the section "Uses of the compound of formula I-1" hereafter.

Preparation of Starting Materials

The compound of formula I-1 can be prepared as summarized in Scheme 1 hereafter.

Scheme 1

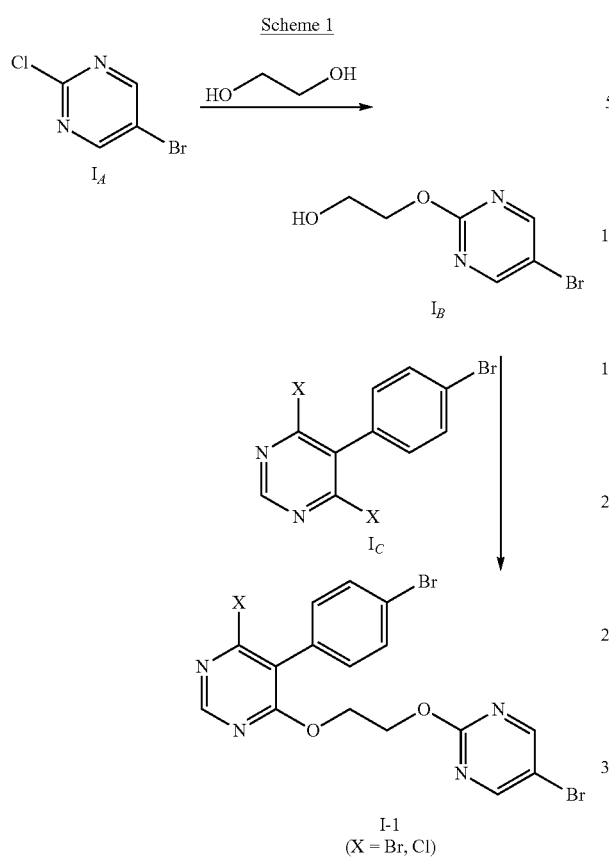

5-bromo-2-chloropyrimidine (compound IA) can be reacted (Scheme 1) with ethylene glycol in the presence of a base (e.g. tBuOK or DBU), affording 2-((5-bromopyrimidin-2-yl)oxy)ethanol (compound IB). Another method for obtaining the compound IB would be to perform the reaction of 5-bromo-2-chloropyrimidine with 2-(tert-butoxy)ethanol in the presence of a base such as tBuOK and then the removal of the tert-butyl protecting group either by using conc. aq. HCl or by using formic acid followed by aq. NaOH; yet a further method for obtaining the compound IB would be to proceed as described in Kokatla and Lakshman, *Org. Lett.* (2010), 12, 4478-4481. The compound IB can then be reacted, in a polar aprotic solvent in the presence of a base, with 5-(4-bromophenyl)-4,6-dichloropyrimidine or 5-(4-bromophenyl)-4,6-dibromopyrimidine (compound of formula $I_C$ wherein X is Br or Cl), thus providing the compound of formula I-1 wherein X is Br or Cl. To obtain the compound of formula I-1 wherein X is F, the compound of formula I-1 wherein X is Br or Cl can be reacted with TBAF hydrate in the presence or the absence of a base in a polar aprotic solvent. The compound of formula $I_C$ wherein X is Br or Cl can be prepared by methods similar either to those described in Bolli et al., *J. Med. Chem.* (2012), 55, 7849-7861 or to those described in WO 2010/091824.

The compound of formula I-2 is either commercial (when R is H) or can be prepared by methods similar to those described in Bolli et al., *J. Med. Chem.* (2012), 55, 7849-7861 for obtaining the compound of formula I-2 wherein R is n-propyl (when R is $(C_1-C_6)$alkyl or benzyl).

Uses of the Compound of Formula I-1

The compound of formula I-1 wherein X is Br or Cl can notably be used either for obtaining directly the compounds of formula I (see for example embodiment 1) above) or for obtaining the compound of formula I-1 wherein X is F (by reaction with TBAF in the presence or the absence of a base). The compound of formula I-1 wherein X is F can notably be used for obtaining the compounds of formula I (see for example embodiment 1) above).

ABBREVIATIONS AND TERMS USED IN THIS TEXT

Abbreviations

The following abbreviations are used throughout the specification and the examples:
Ac acetyl
approx. approximately
aq. aqueous
BOP 1H-benzotriazol-1-yloxy-tris(dimethylamino)phosphonium hexafluorophosphate
DAD diode array detection
DBU 1,8-diazabicyclo[5.4.0]undec-7-ene
DCM dichloromethane
DMAC dimethylacetamide
DME 1,2-dimethoxyethane
DMF dimethylformamide
DMSO dimethylsulfoxide
EA ethyl acetate
eq. equivalent(s)
Fmoc 9-fluorenylmethoxycarbonyl
GC gas chromatography
Hept heptane
iPrOH isopropanol
iPrOAc isopropyl acetate
IT internal temperature
LC-MS liquid chromatography-mass spectroscopy
MeCN acetonitrile
MS mass spectroscopy
NMP N-methyl-2-pyrrolidone
org. organic
RT room temperature
% a/a percent determined by area ratio
TBAF tetra-n-butylammonium fluoride
TFA trifluoroacetic acid
THF tetrahydrofuran
$t_R$ retention time Definitions of Particular Terms Used in this Text The following paragraphs provide definitions of the various chemical moieties for the compounds according to the invention as well as other particular terms used in this text and are intended to apply uniformly throughout the specification and claims, unless an otherwise expressly set out definition provides a broader or narrower definition:

The term "alkyl" refers to a straight or branched chain alkyl group containing from one to six carbon atoms. The term "$(C_1-C_x)$alkyl" (x being an integer) refers to a straight or branched chain alkyl group containing 1 to x carbon atoms. For example, a $(C_1-C_6)$alkyl group contains from one to six carbon atoms. Representative examples of alkyl groups include methyl, ethyl, n-propyl, iso-propyl, n-butyl, iso-butyl, sec-butyl and tert-butyl.

The term "halogen" refers to fluorine, chlorine, bromine or iodine, and preferably to fluorine or chlorine.

The expression "polar aprotic solvent" refers to a solvent which does not have an acidic hydrogen and has an electric dipole moment of at least 1.5 Debye. Representative examples of polar aprotic solvents include MeCN, chlorobenzene, EA, iPrOAc, THF, NMP, dioxane, DMAC, DME, DMF, DMSO or sulfolane.

The expression "polar mixture of aprotic solvents" refers to a mixture of solvents which do not have an acidic hydrogen, whereby said mixture has an electric dipole moment of at least 1.5 Debye. Representative examples of mixtures of aprotic solvents include, but are not limited to: a mixture of two solvents, whereby the first of these solvents is selected from the group consisting of toluene and DCM and the second of these solvents is selected from the group consisting of MeCN, chlorobenzene, EA, iPrOAc, THF, NMP, dioxane, DMAC, DME, DMF, DMSO and sulfolane; or a mixture of toluene, DCM and a solvent selected from the group consisting of MeCN, chlorobenzene, EA, iPrOAc, THF, NMP, dioxane, DMAC, DME, DMF, DMSO and sulfolane.

The expression "room temperature" as used herein refers to a temperature of from 20 to 30° C., and preferably 25° C.

Unless used regarding temperatures, the term "about" or "approximately" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Particular embodiments of the invention are described in the following Examples, which serve to illustrate the invention in more detail without limiting its scope in any way.

EXAMPLES

All temperatures given are external temperatures and are stated in ° C. Compounds were characterized by $^1$H-NMR (400 MHz) or $^{13}$C-NMR (100 MHz) (Bruker; chemical shifts δ are given in ppm relative to the solvent used; multiplicities: s=singlet, d=doublet, t=triplet; p=pentet, hex=hexet, hept=heptet, m=multiplet, br.=broad, coupling constants are given in Hz); by GC-MS; by LC-MS (Finnigan Navigator with HP 1100 Binary Pump and DAD).

Parameters of the LC-MS Method 1:

| | |
|---|---|
| Injection volume: | 2 μL |
| Column: | Kinetex C18, 2.6 μm, 2.1 × 50 mm |
| Column flow rate: | 1 mL/min |
| Eluents: | Eluent A: water + 0.08% TFA |
| | Eluent B: MeCN + 0.012% TFA |
| Gradient: | 2.0 min    95% B |
| | 2.8 min    95% B |
| | 3.0 min    5% B |
| Temperature: | 40° C. |
| Detector wavelength | 210 nm |

Parameters of the LC-MS Method 2:

| | |
|---|---|
| Injection volume: | 0.40 μL |
| Column: | Hypersil Gold, 1.7 μm, 3.0 × 50 mm |
| Column flow rate: | 1.2 mL/min |
| Eluents: | Eluent A: water + 0.04% TFA |
| | Eluent B: MeCN |
| Gradient: | 0.0 min    2% B |
| | 4.5 min    90% B |
| | 5.7 min    90% B |
| | 6.0 min    2% B |
| Temperature: | 40° C. |
| Detector wavelength | 210 nm |

Parameters of the LC-MS Method 3:

| | |
|---|---|
| Equipment | HPLC system, Acquity UPLC Waters with data acquisition system (i.e. Empower) |
| Stationary phase | Waters Acquity UPLC BEH C18 (Part No. 186002350) |
| Column | 50 mm × 2.1 mm, 1.7 μm |
| Column temperature | 20° C. |
| Temperature autosampler | 5° C. |
| Detection wavelength | 260 nm, resolution 1.2 nm |
| Mobile phase | Gradient mode |
| | Mobile phase A: H2O/ACN/TFA (95/5/0.1% v/v) |
| | Mobile phase B: ACN/H2O/TFA (95/5/0.1% v/v) |
| Pressure (for information) | ca. 580 bar |

| Gradient composition | Time (min) | % A | % B | Flow (mL/min) |
|---|---|---|---|---|
| | 0 | 90 | 10 | 0.6 |
| | 5 | 40 | 60 | 0.6 |
| | 7 | 0 | 100 | 0.6 |
| | 7.5 | 0 | 100 | 0.6 |
| | 7.6 | 90 | 10 | 0.6 |
| | 9 | 90 | 10 | 0.6 |

| | |
|---|---|
| Injection volume | 1 μL |
| Run time | 9 min |
| Chromatogram time | 9 min |

Example 1: 5-(4-bromophenyl)-4-(2-((5-bromopyrimidin-2-yl)oxy)ethoxy)-6-chloropyrimidine Variant I:

5-(4-bromophenyl)-4,6-dichloropyrimidine (26.7 g; 88.0 mmol) and 2-((5-bromopyrimidin-2-yl)oxy)ethanol (20 g; 91.3 mmol; 1.04 eq.; prepared as described in Kokatla and Lakshman, Org. Lett. (2010), 12, 4478-4481) were suspended in toluene (266 mL). KOtBu (11.3 g, 101 mmol, 1.15 eq.) was added portionwise at 10-20° C. The resulting mixture (white suspension to orange mixture) was stirred at 20-25° C. After 1.5 h, 40% aq. citric acid (100 mL) was added until pH is around 2-3. The layers were separated. The org. phase was washed 3 times with water (100 mL) and concentrated to dryness to give crude title compound as an orange oil (46 g). MeOH (65 mL) was added and a yellow precipitate was formed. More MeOH (160 mL) was added and the resulting suspension was slurried under reflux for 30 min. It was cooled to 20-25° C. It was filtered off, rinsed with MeOH and dried under vacuum to yield the title compound as a white powder (36.3 g; 85% yield).

$^1$H-NMR (CDCl$_3$) δ: 8.54 (s, 1H); 8.50 (s, 2H); 7.55-7.51 (m, 2H); 7.22-7.18 (m, 2H); 4.78-4.74 (m, 2H); 4.66-4.64 (m, 2H).

[M+1]$^+$=485 and 487.

LC-MS (method 1): t$_R$=1.97 min; 96.5% a/a,

Variant II:

5-(4-bromophenyl)-4,6-dichloropyrimidine (100 g; 329 mmol) and 2-((5-bromopyrimidin-2-yl)oxy)ethanol (72.1 g; 329 mmol; 1 eq.; prepared as described in Kokatla and Lakshman, *Org. Lett.* (2010), 12, 4478-4481) were suspended in toluene (1 L). 1,8-diazabicyclo[5.4.0]undec-7-ene (73.6 mL; 493 mmol; 1.5 eq.) was added dropwise at 20-40° C. The resulting mixture was stirred at 80-85° C. for 5 h. It was allowed to cool to 20-25° C. Water (1 L) was added. The layers were separated. The org. phase was washed with a 10% aq. solution of citric acid (1 L). The layers were separated and the aq. phase was back-extracted with toluene (500 mL). The combined org. extracts were washed with water. The toluene was exchanged with iPrOH under vacuum at 50-55° C. The resulting mixture was stirred at 50-55° C. for 2 h. It was cooled to 20-25° C. over 2 h, filtered off and rinsed with iPrOH to afford the title compound as a white powder (136 g; 85% yield).

The product had NMR data equivalent to those obtained for the product of Variant I.

Example 2: 5-(4-bromophenyl)-4-(2-((5-bromopyrimidin-2-yl)oxy)ethoxy)-6-fluoropyrimidine Variant I:

The compound of Example 1 (20.0 g; 41.1 mmol; 1.0 eq.) and cesium fluoride (7.5 g; 49.3 mmol; 1.2 eq.) were suspended in DMSO (200 mL). It was heated to 70-75° C. over 4 h. The brown reaction mixture was cooled to 20-25° C. It was diluted with EA (140 mL), washed with water (140 mL), a 10% aq. citric acid solution (140 mL) and brine (140 mL).

It was concentrated to dryness to afford the title compound as a crude yellow solid. This material was suspended in iPrOH (40 mL) and heated to reflux for 10 min. THF (5 mL) was added and the resulting mixture was heated to reflux for 10 min whereby a clear solution was obtained. It was allowed to cool on its own to 20-25° C. while being seeded at IT=43° C. It was filtered off, rinsed with iPrOH (5 mL) and dried under vacuum to afford the title product as a yellow solid (17.9 g, 93% yield).

$^1$H-NMR (CDCl$_3$) δ: 8.52 (s, 2H); 8.47 (d, J=1.9 Hz, 1H); 7.55-7.51 (m, 2H); 7.36-7.33 (m, 2H); 4.84-4.82 (m, 2H), 4.72-4.70 (m, 2H).

[M+1]$^+$=471 and 473.

LC-MS (method 1): $t_R$=1.92 min; 100% a/a,

Variant II:

The compound of Example 1 (5.0 g; 10.3 mmol; 1.0 eq.) and TBAF.3H$_2$O (5.4 g; 17.0 mmol; 1.7 eq.) were suspended in DMSO (50 mL). The mixture was stirred at 20-25° C. for 6 h. EA was added (50 mL), followed by a sat. aq. solution of CaCl$_2$ (10 mL). The layers were separated and the org. phase was washed 3 times with brine (50 mL each time), then once with water (25 mL). The org. phase was concentrated under reduced pressure to dryness. The residue was recrystallized from iPrOH (10 mL) and THF (1.25 mL) to afford the title product as a white powder (3.2 g, 66% yield).

The product had NMR data equivalent to those obtained for the product of Variant I.

LC-MS (method 1): $t_R$=1.92 min; 88% a/a.

Variant III:

A reactor was charged with compound of Example 1 (600 g; 1.23 mol; 1.0 eq.), cesium fluoride (562 g; 3.69 mol; 3.0 eq.), DMSO (3 L) and toluene (1.2 L). The toluene was distilled off, and the remaining mixture was stirred at 70° C. for 2 h. After cooling to RT, EA (2.4 L) and water (2.4 L) were added. The layers were separated, and the org. layer was successively washed with 7.5% w/v CaCl$_2$ solution (2.4 L), brine (2.4 L) and water (3 L). The solvent was exchanged to iPrOH (2.4 L), THF (150 mL) was added, and the slurry was heated to reflux. The resulting solution was slowly cooled to room temperature. Filtration, washing with iPrOH (0.6 L) and drying afforded the title compound as an off-white solid (526 g, 91% yield).

LC-MS (method 3): $t_R$=5.27 min; 99.3% purity.

Example 3: preparation of {5-(4-bromo-phenyl)-6-[2-(5-bromo-pyrimidin-2-yloxy)-ethoxy]-pyrimidin-4-yl}-sulfamide Variant I:

The compound of Example 1 (25 g; 51.4 mmol), sulfamide (5.4 g; 56.5 mmol; 1.1 eq.), TBAF.3H$_2$O (48.6 g, 154 mmol, 3 eq.) and potassium carbonate (21.3 g, 154 mmol, 3 eq.) were suspended in DMSO (250 mL) at 20-25° C. The mixture was heated to 70-75° C. for 1 h. At this point, LC-MS indicated complete conversion. The reaction mixture was cooled to 10-15° C. Water (200 mL) and DCM (350 mL) were added (caution: exotherm). The layers were separated and the org. phase was washed twice with water (200 mL). It was washed with 20% aq. citric acid (200 mL) and water (200 mL; pH around 3-4). The org. phase was concentrated to dryness to afford the crude title compound as an orange oil. This material was adsorbed on Isolute (30 g) with DCM. This residue was purified over silica gel (300 g) using EA as solvent (600 mL) to give a white foam (26 g). The latter was dissolved in EA (50 mL) and heated to reflux. Spontaneous crystallization was observed. It was heated to reflux for 10 min. More EA (50 mL) was added. It was allowed to cool to 20-25° C., filtered, rinsed with EA and dried under vacuum to give the title compound as a white powder (12.6 g; 45% yield).

The product had NMR data equivalent to those reported in the supporting information associated with Bolli et al., *J. Med. Chem.* (2012), 55, 7849-7861.

Variant II:

The compound of Example 1 (10 g; 20.6 mmol), sulfamide (2.2 g; 56.5 mmol; 1.1 eq.), TBAF.3H$_2$O (16.2 g, 51.4 mmol, 2.5 eq.) and potassium carbonate (7.1 g; 51.4 mmol; 2.5 eq.) were suspended in DMSO (50 mL) at 20-25° C. The mixture was heated to 70-75° C. for 1 h. At this point, LC-MS indicated complete conversion. The reaction mixture was cooled to 10-15° C. Water (100 mL) and DCM (100 mL) were added (caution: exotherm). The layers were separated and the org. phase was washed with brine (to pH=11; 100 mL), with 40% aq. citric acid (to pH=3; 100 mL), twice with brine (100 mL) and finally with water (50 mL). The mixture was concentrated to a residual volume of approx. 50 mL. It was seeded at 20-25° C. Crystallization occurred slowly at 20-25° C. It was cooled to 4° C. and stirred for 1 h. It was filtered off, washed with cold DCM (10 mL) and dried under vacuum to afford the title compound as a white solid (7.1 g, 63% yield).

The product had NMR data equivalent to those reported in the supporting information associated with Bolli et al., *J. Med. Chem.* (2012), 55, 7849-7861.

Variant III:

The compound of Example 1 (100 g; 206 mmol), sulfamide (21.7 g; 226 mmol; 1.1 eq.), TBAF.3H$_2$O (162 g; 514 mmol; 2.5 eq.) and potassium carbonate (71 g; 514 mmol; 2.5 eq.) were suspended in DMSO (500 mL) at 20-25° C. The mixture was heated to 70-75° C. for 2 h. At this point, LC-MS indicated complete conversion. The reaction mixture was cooled to 10-15° C. Water (1 L) and EA (1 L) were added (caution: exotherm). The layers were separated and the org. phase was washed with brine (1 L). It was washed with a sat. CaCl₂ solution (1 L) followed by 40% aq. citric acid (1 L), 3 times with brine (1 L) and finally with water (0.5 L). The mixture was seeded at RT and allowed to cool to 0° C. over 15 h. It was filtered off, washed with cold EA (100 mL) and dried under vacuum to afford the title compound as a white solid (52 g; 46% yield).

The product had NMR data equivalent to those reported in the supporting information associated with Bolli et al., *J. Med. Chem.* (2012), 55, 7849-7861.

LC-MS (method 2): $t_R$=2.80 min; 98.5% a/a.

Variant IV:

The compound of Example 2 (2 g; 4.25 mmol), sulfamide (0.45 g; 4.68 mmol; 1.1 eq.) and potassium carbonate (1.5 g; 10.6 mmol; 2.5 eq.) were suspended in DMSO (10 mL). It was heated to 70° C. for 15 h. The mixture was cooled to 20-25° C. A 40% aq. solution of citric acid was added dropwise (20 mL), followed by DCM (20 mL). The layers were separated and the org. phase was washed with brine (20 mL) and water (10 mL). The combined org. layers were concentrated under reduced pressure to a residual volume of approx. 20 mL. It was cooled to 0-5° C., washed with cold DCM (5 mL), filtered and dried under reduced pressure (40° C., 10 mbar) to afford the title compound as a white solid (1.51 g, 65% yield). The product had NMR data equivalent to those reported in the supporting information associated with Bolli et al., *J. Med. Chem.* (2012), 55, 7849-7861.

LC-MS (method 1): $t_R$=1.59 min; 99.0% a/a.

Variant V:

The compound of Example 2 (2 g; 4.25 mmol), sulfamide (0.58 g; 6.0 mmol; 1.4 eq.) cesium fluoride (1.6 g; 10.4 mmol; 1.5 eq.) and potassium carbonate (1.8 g; 12.7 mmol; 3 eq.) were suspended in DMSO (10 mL) at 20-25° C. The mixture was heated to 70-75° C. for 15 h. At this point, LC-MS (method 1) indicated complete conversion. The reaction mixture was cooled to 10-15° C., DCM (20 mL) and 30% aq. citric acid solution (20 mL) were added. The layers were separated and the org. phase was washed twice with 30% aq. citric acid before being concentrated to dryness. The residue was taken up in DCM (10 mL), slurried for 30 min and filtered off to afford the title compound as a white solid. (400 mg; 17% yield).

The product had NMR data equivalent to those reported in the supporting information associated with Bolli et al., *J. Med. Chem.* (2012), 55, 7849-7861.

LC-MS (method 1): $t_R$=1.57 min; 98.4% a/a.

Variant VI:

A mixture of the compound of Example 2 (100 g; 0.213 mol; 1.0 eq.), sulfamide (40.9 g; 0.425 mol; 2.0 eq.), K₂CO₃ (147 g) and DMSO (500 mL) was heated to 70° C. for 3 h. After cooling to RT, the mixture was filtered and the filter cake washed with EA/iPrOAc 1:1 (300 mL). The solution was treated with charcoal and rinsed with EA/iPrOAc 1:1 (300 mL), followed by addition of 1M aq. NaOAc solution (500 mL). The aq. phase was washed with EtOAc/iPrOAc 1:1 (500 mL). Slow addition of 1M H₂SO₄ (200 mL) led to crystallization of the crude product, which was washed twice with water (2×1 L). The crude material was slurried in water (1 L) at RT for 3 h. After filtration and washing with water (1 L), the material was dried to furnish the title compound as an off-white solid (75 g, 65% yield).

The product had NMR data equivalent to those reported in the supporting information associated with Bolli et al., *J. Med. Chem.* (2012), 55, 7849-7861.

LC-MS (method 3): $t_R$=3.77 min; 99.5% purity.

Variant VII:

A mixture of the compound of Example 1 (10.00 g; 20.6 mmol; 1.0 eq.), cesium fluoride (9.378 g; 61.7 mmol; 3.0 eq.) and DMSO (25 mL) was stirred at 70° C. for 2.5 h. Potassium carbonate (14.2 g; 103 mmol; 5.0 eq.) and sulfamide (3.95 g; 41.1 mmol; 2.0 eq.) were added and the heating continued for another 3 h. After cooling to RT, the mixture was filtered and the filter cake washed with EA/iPrOAc 1:1 (50 mL). The combined filtrate was acidified with 1M H₂SO₄ (10 mL) to furnish a cloudy solution. Addition of water (50 mL) led to formation of a suspension. The solid was filtered, washed twice with water (2×100 mL) and dried to give the title compound as a white powder (8.6 g; 77% yield).

The product had NMR data equivalent to those reported in the supporting information associated with Bolli et al., *J. Med. Chem.* (2012), 55, 7849-7861.

Example 4: preparation of propyl-sulfamic acid {5-(4-bromo-phenyl)-6-[2-(5-bromo-pyrimidin-2-yloxy)-ethoxy]-pyrimidine-4-yl}-amide (macitentan)

Variant I:

The compound of Example 1 (10 g; 20.6 mmol), propyl-sulfamide (3.1 g; 22.6 mmol; 1.1 eq.; prepared as described in Bolli et al., *J. Med. Chem.* (2012), 55, 7849-7861), TBAF.3H₂O (19.5 g; 61.7 mmol; 3 eq.) and potassium carbonate (8.5 g; 61.7 mmol; 3 eq.) were suspended in DMSO (100 mL). The mixture was heated to 100° C. for 1 h and then cooled to 20-25° C. Water (100 mL) and DCM (100 mL) were added. The org. layer was washed 3 times with water (100 mL each time), 20% aq. citric acid (100 mL) and water (100 mL) before being concentrated under reduced pressure to dryness. The residue was suspended in EA (15 mL) and heated to reflux. Hept (30 mL) was added. The mixture was allowed to cool to 20-25° C. on its own. The precipitate was filtered off and rinsed with Hept (10 mL). The beige solid thus collected (11.0 g) was recrystallized from EA (30 mL) and Hept (25 mL) to afford the title compound as a white solid (6.4 g; 53% yield).

The product had MS and NMR data equivalent to those reported in Bolli et al., *J. Med. Chem.* (2012), 55, 7849-7861.

LC-MS (method 1): $t_R$=1.89 min; 100% a/a.

Variant II:

The compound of Example 2 (2 g; 4.25 mmol), propyl-sulfamide (735 mg; 5.32 mmol; 1.2 eq.; prepared as described in Bolli et al., *J. Med. Chem.* (2012), 55, 7849-7861), cesium fluoride (2.0 g; 12.8 mmol; 3 eq.) and potassium carbonate (1.7 g; 12.8 mmol; 3 eq.) were suspended in DMSO (20 mL) at 20-25° C. The mixture was heated to 70-75° C. for 15 h. Water (20 mL) and DCM (20 mL) were added. The layers were separated and the org. phase was washed with 30% aq. citric acid (20 mL) before being concentrated to dryness.

The residue was recrystallized from toluene to yield the title compound as a white powder (600 mg; 24% yield).

The product had MS and NMR data equivalent to those reported in Bolli et al., *J. Med. Chem.* (2012), 55, 7849-7861.

LC-MS (method 1): $t_R$=1.83 min; 96.7% a/a.

Example 5: preparation of benzyl-sulfamic acid {5-(4-bromo-phenyl)-6-[2-(5-bromo-pyrimidin-2-yloxy)-ethoxy]-pyrimidine-4-yl}-amide The compound of Example 2 (14 g; 28.7 mmol), benzyl-sulfamide potassium salt (7.09 g; 31.6 mmol; 1.1 eq.;

prepared as described in Bolli et al., J. Med. Chem. (2012), 55, 7849 7861), TBAF.3H2O (27.2 g; 86.2 mmol; 3 eq.) and potassium carbonate (15.9 g; 115 mmol; 4 eq.) were suspended in DMSO (140 mL) at 20 25° C. The mixture was heated to 100 105° C. for 1 h. At this point, LC-MS (method 1) indicated complete conversion. The reaction mixture was cooled to 10-15° C. Water (140 mL) and DCM (140 mL) were added. The layers were separated and the org. layer was washed twice with water (140 mL), 10% aq. citric acid (140 mL) and with water (140 mL). It was concentrated under reduced pressure. The oily residue was purified by flash chromatography over silica gel (eluent: Hept/EA) to afford the title compound as a white solid (4.75 g, 26% yield).

The product had NMR data equivalent to those reported in Bolli et al., J. Med. Chem. (2012), 55, 7849-7861.

[M+1]+=635 and 637.

LC-MS (method 1): tR=1.94 min; 81.0% a/a.

The invention claimed is:

1. A method for manufacturing a compound of formula I

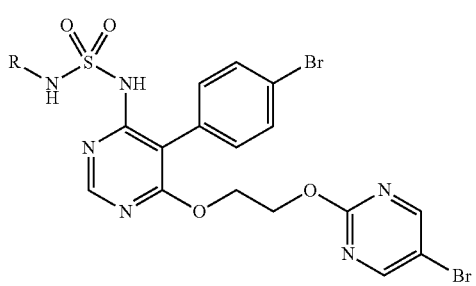

wherein R is H, or a salt thereof, said method comprising the reaction of the compound of formula I-1

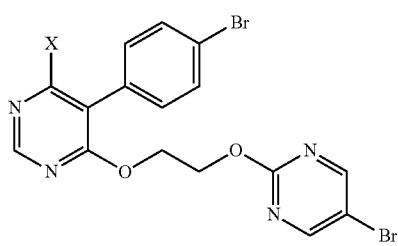

wherein X is bromine, chlorine or fluorine, with the compound of formula I-2

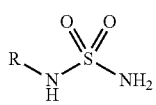

wherein R is H, or a salt of said compound of formula I-2, said reaction being performed in the presence of a base in a polar aprotic organic solvent or a polar mixture of aprotic organic solvents, and, when X is bromine or chlorine, in the presence of tetra-n-butyl ammonium fluoride hydrate or cesium fluoride.

2. The method of claim 1, wherein the base is NaOH, KOH, 1,8-diazabicyclo[5.4.0]undec-7-ene, triethylamine, potassium text-butylate, $Na_2CO_3$ $K_2CO_3$ or $Cs_2CO_3$.

3. The method of claim 2, wherein the base is $K_2CO_3$.

4. The method of claim 1, wherein the polar aprotic organic solvent or polar mixture of aprotic organic solvents comprises dimethylsulfoxide.

5. The method of claim 4, which is performed using dimethylsulfoxide as solvent.

6. The method of claim 1, wherein X is chlorine and the reaction of the compound of formula I-1 with the compound of formula I-2 is performed in the presence of tetra-n-butyl ammonium fluoride hydrate and using dimethylsulfoxide as solvent.

7. A compound of formula I-1

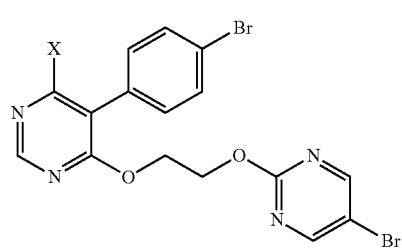

wherein X is fluorine;
or a salt of said compound.

8. A method of manufacturing a compound of formula I,

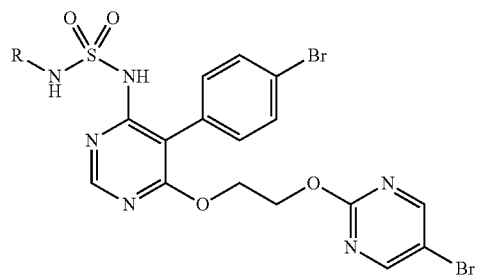

wherein R is H, or a salt thereof, comprising reacting the compound of formula I-1

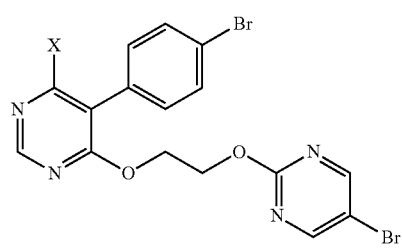

wherein X is chlorine, or a salt thereof; with a fluorination agent.

9. A method for manufacturing the compound of formula I

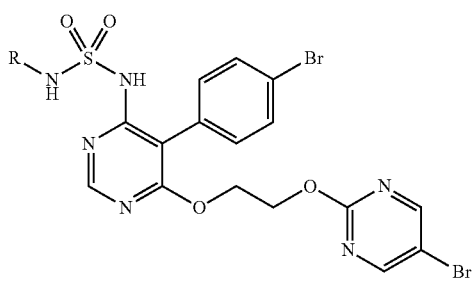

wherein R is H, or for manufacturing a salt thereof, said method comprising reacting a compound of formula I-1$_{Cl}$

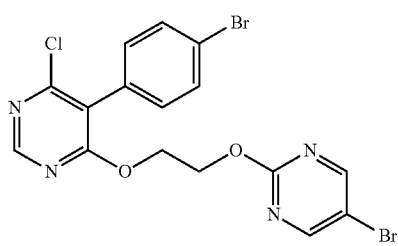

or a salt thereof, with tetra n-butyl ammonium fluoride hydrate or cesium fluoride in the presence of a base in a polar aprotic organic solvent or a polar mixture of aprotic organic solvents, to yield the compound of formula I-1$_F$

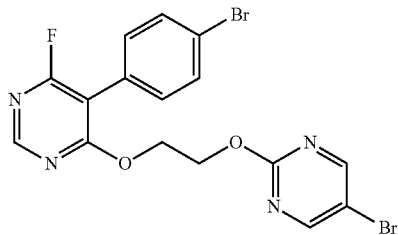

and
reacting the compound of formula I-1$_F$ with a compound of formula I-2

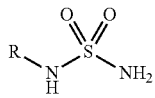

wherein R is H, or a salt thereof, in the presence of a base in a polar aprotic organic solvent or a polar mixture of aprotic organic solvents, to yield said compound of formula I or a salt thereof.

10. The method of claim 9, wherein the compound of formula I-1$_{Cl}$ is reacted with cesium fluoride.

11. The method of claim 8, wherein the fluorination agent is tetra-n-butyl ammonium fluoride hydrate.

12. A method for manufacturing a compound of formula I

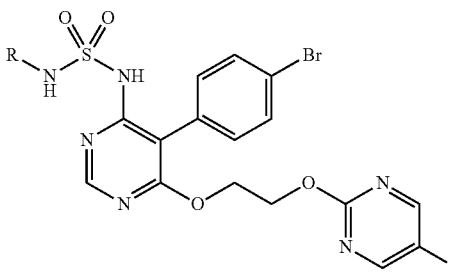

wherein R is n-propyl, or a salt thereof, said method comprising reacting a compound of formula I-1

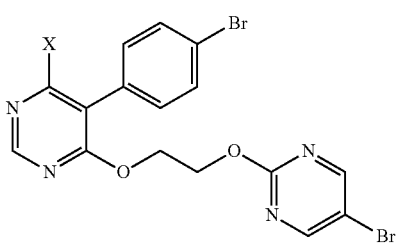

wherein X is bromine, chlorine or fluorine, with a compound of formula I-2

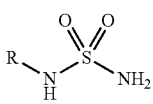

wherein R is n-propyl, or a salt of said compound of formula I-2, said reaction being performed in the presence of a base in a polar aprotic organic solvent or a polar mixture of aprotic organic solvents, and, when X is bromine or chlorine, in the presence of tetra-n-butyl ammonium fluoride hydrate or cesium fluoride.

13. The method of claim 12, wherein the base is NaOH, KOH, 1,8-diazabicyclo[5.4.0]undec-7-ene, triethylamine, potassium tort-butylate, Na$_2$CO$_3$ K$_2$CO$_3$ or Cs$_2$CO$_3$.

14. The method of claim 13, wherein the base is K$_2$CO$_3$.

15. The method of claim 12, wherein the polar aprotic organic solvent or polar mixture of aprotic organic solvents comprises dimethylsulfoxide.

16. The method of claim 15, wherein the dimethylsulfoxide is used as a solvent.

17. The method of claim 12, wherein X is chlorine and the reaction of the compound of formula I-1 with the compound of formula I-2 is performed in the presence of tetra-n-butyl ammonium fluoride hydrate and using dimethylsulfoxide as solvent.

18. A method of manufacturing a compound of formula I,

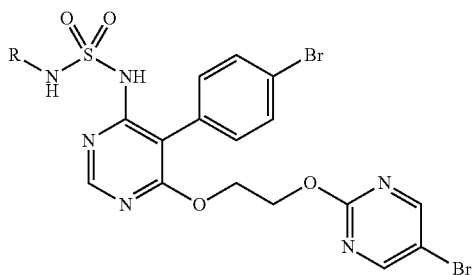

wherein R is n-propyl, or a salt thereof, comprising reacting the compound of formula I-1

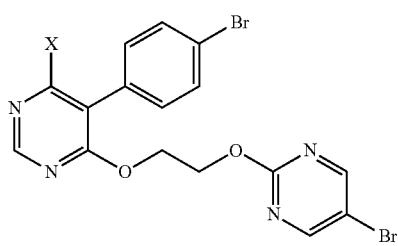

with a fluorination agent.

19. A method for manufacturing the compound of formula I

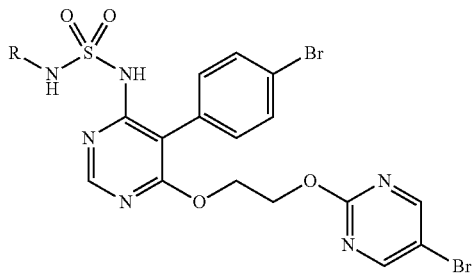

wherein R is n-propyl, or for manufacturing a salt thereof, said method comprising reacting a compound of formula I-1$_{Cl}$

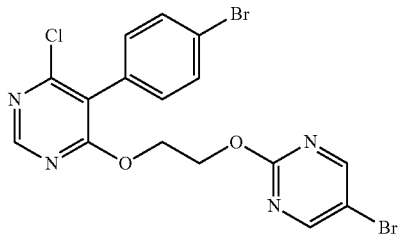

or a salt thereof, with tetra n-butyl ammonium fluoride hydrate or cesium fluoride in the presence of a base in a polar aprotic organic solvent or a polar mixture of aprotic organic solvents, to yield the compound of formula I-1$_F$

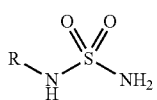

and
reacting the compound of formula I-1$_F$ with a compound of formula I-2 wherein R is n-propyl, or a salt thereof, in the presence of a base in a polar aprotic organic solvent or a polar mixture of aprotic organic solvents, to yield said compound of formula I or a salt thereof.

20. The method of claim 19, wherein the compound of formula I-1$_{Cl}$ is reacted with cesium fluoride.

21. The method of claim 18, wherein the fluorination agent is tetra-n-butyl ammonium fluoride hydrate.

* * * * *